United States Patent [19]
Hill et al.

[11] Patent Number: 5,726,195
[45] Date of Patent: Mar. 10, 1998

[54] AMINOACYL ADENYLATE MIMICS AS NOVEL ANTIMICROBIAL AND ANTIPARASITIC AGENTS

[75] Inventors: Jason M. Hill, Newtonville; Guixue Yu, Wakefield; Youe-Kong Shue, Sudbury; Thomas M. Zydowsky, Cambridge, all of Mass.; Julius Rebek, La Jolla, Calif.

[73] Assignee: Cubist Pharmaceuticals, Inc., Cambridge, Mass.

[21] Appl. No.: 683,809

[22] Filed: Jul. 16, 1996

Related U.S. Application Data

[60] Provisional application Nos. 60/001,649 Jul. 28, 1995 and 60/014,881, Apr. 4, 1996.

[51] Int. Cl.$^6$ .................. C07D 217/00; C07D 285/00; C07D 257/04; C07D 409/00
[52] U.S. Cl. .................. 514/382; 514/63; 514/307; 514/338; 514/340; 514/361; 514/362; 514/363; 514/365; 514/372; 514/406; 514/407; 514/422; 514/443; 514/444; 514/451; 514/464; 514/465; 546/14; 546/144; 546/148; 546/268.4; 546/283.7
[58] Field of Search .................. 546/14, 144, 148, 546/268.4, 283.7; 548/110, 127, 128, 134, 136, 146, 206, 251, 252, 364.4, 406, 526; 549/4, 58, 60, 214, 414, 435; 514/63, 307, 338, 340, 361, 362, 363, 365, 372, 382, 406, 407, 422, 443, 444, 451, 464, 465

[56] References Cited

U.S. PATENT DOCUMENTS 5,041,567   8/1991   Rogers et al. .................. 549/414

FOREIGN PATENT DOCUMENTS

| 2 284 811 A | 6/1995 | United Kingdom ......... C07H 19/167 |
| 2 287 464 A | 8/1995 | United Kingdom ......... C07H 19/167 |
| WO-A-95 05384 | 2/1995 | WIPO ..................... C07D 495/00 |

OTHER PUBLICATIONS

Cassio, D., et al., "Selective Inhibition of Aminoacyl Ribonucleic Acid Synthetases by Aminoalkyl Adenylates", Biochemistry 6(3):827–835 (1967).
Mantell, S., et al., "3–Hydroxymuscarines from L–Rhamnose", Tetrahedron 49 (16):3343–3358 (1993).
Acton, E., et al., "Synthesis of C–Nucleoside Analogues by 1,3–Dipolar Addition of a 1–Diazo–sugar to Acetylenes", J. of the Chemical Communications; 313–314 (1970).
Osada, H., et al. "Mechanism of Action and Selective Toxicity of Ascaycin, a Nucleoside Antibiotic"; Antimicrobial Agents and Chemotherapy 27(2): 230–233 (1985).
Clark, C.M., et al. "Affinity Chromatography and Aminoacyl–Transfer Ribonucleic Acid Synthetases"; Biochem Journal 167: 405–417 (1977).
Rainey, P., et al. "Purification of L–Isoleucyl t–RNA Synthetase By Affinity Chromatography"; Preparative Biochemistry 4(3): 227–241(1974).
Judoka, B., et al. "Oligonucleotide–Peptides . . . "; J. of Carbohydrates Nucleosides Nucleotides 6(4); 333–357 (1979).
Chu, B.C.F., et al. "Derivatization of Unprotected Polynucleotides"; Nucleic Acids Research 11(18): 6513–6529 (1983).
Piel, N., et al. "Synthesis of Modified Tryptophanyl–Adenylates and of Modified Adenosine–Triphosphates and Their Use as Tools for Elucidation of the Mechanism of Tryptophanyl–tRNA Synthetase from Yeast"; Bioorganic Chemistry 12: 18–33 (1983).
Southgate, C.C.B., et al. "Phosphonate Analogues of Aminoacyl Adenylates"; Biochemistry J. 175: 461–465 (1978).
Dorion, C., et al. "Synthesis of an Inhibitor of Glutamyl–tRNA Synthetase"; Bioorg. Med. Chem. Ltrs 3(12): 2699–2702 (1993).
Lawrence, F., et al. "Further Studies of the Action of Methionyl Adenylate on Chick Embryo Fibroblasts"; Biochimica et Biophysica Acta, 476: 16–23 (1977).
Enouf, J., et al. "Comparative Effect of Methioninyl Adenylate on the Growth of *Salmonella typhimurium* and *Pseudomonas aeruginosa*"; Arch. Microbiol. 110: 129–134 (1976).
Robert–Gero, M., et al. "Inhibition by Methioninyl Adenylate of Focus Formation by Rous Sarcoma Virus"; Cancer Research 35: 3571–3576 (1975).
Robert–Gero, M., et al. "Reversible Inhibition By Methioninyl Adenylate of Protein Synthesis and Growth in Chick Embryo Fibroblasts"; Biochemical and Biophysical Research Communication 63(3): 594–600 (1975).
Hecht, S.M., et al. "Interaction of Glycyl–L–phenylalanine with *Escherichia Coli* Phenylalanyl–tRTA Synthetase"; Biochem 13(24): 4967–4975 (1975).
Cassio, D., et al. "Effect of Methioninyl Adenylate on the Growth of *E. coli* K 12"; FEBS Letters 35(1): 112–116 (1973).
Cassio, D., et al. "Selective Inhibition of Aminoacyl Ribonucleic Acid Synthetases by Aminoalkyl Adenylates"; Biochem. 6(3): 827–836 (1967).
Monteihet, C., et al. "Binding of Tyrosine, Adenosine Triphosphate and Analogues to Crystalline Tyrosyl Transfer RNA Synthetase"; J.Mol.Biol. 122: 407–417 (1978).
Khodyreva, S.N., et al. "Phenylalanyl–tRNA Synthetase From *E. Coli* MRE–600: Analysis of the Active Site Distribution on the Enzyme Subunits by Affinity Labelling"; Biochimica et Biophysica Acta 830: 206–212 (1985).

(List continued on next page.)

*Primary Examiner*—Mukund J. Shah
*Assistant Examiner*—Brenda Coleman
*Attorney, Agent, or Firm*—Wolf, Greenfield & Sacks, P.C.

[57] ABSTRACT

Certain novel aminoacyl adenylate mimics are described. An exemplary compound of this invention is [S-(R*,R*)]-3,6-anhydro-1,2-dideoxy-1-[5-[4-[(5-nitro-2-thienyl)ethynyl]phenyl]-2H-tetrazol-2-yl]-D-allo-heptitol 7-(2-amino-3-methyl-1-oxopentyl)sulfamate. These compounds inhibit isoleucyl-tRNA synthetases and are useful as antimicrobial and antiparasitic agents.

50 Claims, No Drawings

OTHER PUBLICATIONS

Krauss, G., et al. "Mechanism of tRNA–Aminoacyl–tRNA Synthetase Recognition Influence of Aminoalkyladenylates"; Biochem. 17(12): 2443–2449 (1978).

Flossdorf, J., et al. "On the Binding of Aminoacyl adenvlates to Isoleucyl–tRNA Synthetase from *Eschereichia coli* MRE 600"; Nucleic Acids Research 4(3): 673–683 (1977).

Santi, D.V., et al. "Tyrosyl Transfer Ribonucleic Acid Synthetase from *Escherichia Coli* B. Analysis of Tyrosine and Adenosine 5'–Triphosphate Binding Sites"; J.Med.Chem. 16(3): 273–280 (1973).

Rouget, P., et al. "Reactions Sequence of Leucine Activation Catalysed by Leucyl–RNA Synthetase"; European J. Biochem 4: 310–314 (1968).

Castro–Pichel, J., et al. "A Facile Synthesis of Ascamycin and Related Analogues"; Tetrahedron 43(2): 383–389 (1987).

Ohrui, H., et al. "C–Glycosyl Nucleosides. V. Some Unexpected Observations on the Relative Stabilites of Compounds Containing Fused Five–Membered Rings with Epimerizable Substituents"; J.Am.Chem.Soc. 97(16):4602–4613 (1975).

Utimoto. K., et al. "A Facile Preparation of 0–Acylated β–D–Ribofuranosyl Cyanide, An Important Intermediate of C–Nucleoside Synthesis"; Tetrahedron Letters 23(2): 237–238 (1982).

Sandrin, E., et al. "Synthese d'esters adenosine–5'–phosphoriques d'amino–alcools, comme inhibiteurs potentiels de l'activation des acides amines'"; Helv. Chimica Acta. 49(13): 76–82 (1966).

Khomu–ov, R.M., et al. "Organophosphorus Analogs of Biologically Active Compounds"; Bioorg.Khim. 56–62 (1979).

Yakovleva, G.M., et al. "Organophosphorous Analogues of Biologically Active Compounds";Bioorg.Khim 10(2): 213–219 (1984).

Cross, C.L., et al. "Rules For The Nomenclature Of Organic Chemistry Section E: Sterochemistry"; Pure & Appl. Chem. 45:11–30 (1976).

Isono, K., et al., "Ascamycin and Dealanylascamycin, Nucleoside Antibiotics From Streptomyces sp."; Journal Of Antibiotics 670–672 (1984).

Cacciapuot, M., et al. "Nuovi Nucleosidi 5'–Solforati Quali Inibitori Della Biosintesi Delle Poliammine"; Boll. Soc., It. Biol. Sper. 56: 238–244 (1980).

Brown, P., et al. "Investigation Of The Active Site Of *B.stearothermophilus* Tyrosyl t–RNA Synthetase By The Synthesis of Tyrosinyl Adenylate Analogues"; Smithkline Beecham: poster presented at the 16th International tRNA Workshop Madison, WI (May 27–Jun. 1, 1995.

Gilbart, J., et al. "High–Level Mupirocin Resistance in *Staphylococcus aureus*: Evidence for Two Distinct Isoleuycl–tRNA Synthetases"; Antimicrobial Agents and Chemotherapy, 37(1): 32–38 (1993).

Kern, D., et al. "The Twenty Aminoacyl–tRNA Synthetases From *Escherichia coli*. General Separation Procedure, And Comparison Of The Influence of pH and Divalent Cations on Their Catalytic Activities"; Biochimie. 61: 1257–1272 (1979).

Ohtsuka, E., et al. "New Phosphoramidates As Protecting Groups In Ribooligonucleotides Synthesis"; Nucleic Acids Research. 3(3): 653–660 (1976).

Clement, J. J., et al. "*In Vitro* and *In Vivo* Evaluations of A–80556, a New Fluoroquinolone"; Antimicrob. Agents and Chemotherapy. 38(5): 1071–1078.

Jorgensen, J. H., et al. "Methods for Dilution Antimicrobial Susceptibility Tests for Bacteria that Grow Aerobically–Third Edition: Approved Standard"; National Committee for Clinical Laboratory Standards Document M7–A3 13(25) (1993).

Galgaini, J. N., et al. "References Method for Broth Dilution Antifungal Susceptibility Testing of Yeasts; Proposed Standard"; National Committees for Clinical Laboratory Standards Document M27–P 12(25) (1992).

AMINOACYL ADENYLATE MIMICS AS NOVEL ANTIMICROBIAL AND ANTIPARASITIC AGENTS

CROSS-REFERENCE TO RELATED APPLICATION

This application is related to provisional application Ser. No. 60/001,649 filed Jul. 28, 1995 and provisional application Ser. No. 60/014,881 filed Apr. 4, 1996.

FIELD OF THE INVENTION

This invention relates to the field of isoleucyl-transfer ribonucleic acid (tRNA) synthetase inhibitors, their preparation and their use as antimicrobial and antiparasitic agents.

BACKGROUND OF THE INVENTION

Aminoacyl tRNA synthetases (aaRS) are a family of essential enzymes that are found in virtually every biological cell and are one of the factors responsible for maintaining the fidelity of protein synthesis. They specifically catalyze the aminoacylation of tRNA in a two step reaction:

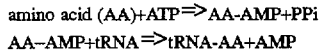

The enzyme binds adenosine triphosphate (ATP) and its specific amino acid to catalyze formation of an aminoacyl adenylate intermediate (AA-AMP) with concomitant release of pyrophosphate (PPi). In the second step, the amino acid is transferred to the 2' or 3' terminus of the tRNA yielding "charged" tRNA and adenosine monophosphate (AMP). The charged tRNA delivers the amino acid to the nascent polypeptide chain on the ribosome.

There are at least twenty essential enzymes in this family for most organism. Inhibition of any of the essential tRNA synthetases disrupts protein translation, ultimately resulting in growth inhibition. Pseudomonic acid A, an antibacterial agent currently used in human therapy, provides clear evidence of the utility of tRNA synthetase inhibitors as useful pharmaceuticals. Pseudomonic acid A binds to isoleucyl-tRNA synthetase, and inhibits isoleucyl adenylate formation in several Gram positive bacterial pathogens such as *Staphylococcus aureus*, resulting in the inhibition of protein synthesis, followed by growth inhibition.

The prior art has focused on designing compounds to elucidate the mechanism and binding sites of tRNA synthetases. Because the aminoacyl adenylate intermediate is not chemically stable, in an effort to study the binding site and the mechanism of tRNA synthetases, investigators have focused on preparing chemically stable aminoacyl adenylate mimics. These compounds resemble the aminoacyl adenylate intermediate; however, structural modifications have been made to the 5' position of the ribose ring. Examples of such modifications include compounds in which the amino acid carbonyl is replaced by a methylene group and structures in which the phosphate moiety has been replaced with a phosphonate, phosphonamide or sulfonamide moiety. There have been no disclosures of stable aminoacyl adenylate mimics for mammalian therapy or which exhibit whole cell activity against organisms.

Modifications to the adenine portion of the aminoacyl adenylate intermediate have not been the focus of much research presumably because the AMP portion of the molecule has been reported to be important for the binding of the adenylate to the binding site of the enzyme [see Cassio, et al., *Biochemistry*, 6 (3), 827–836, (1967)]. More recently, Brown and coworkers have reported that the adenine ring is important to the binding of related compounds to a tRNA synthetase, since an analogue of tyrosinyl adenylate, in which the adenine ring is replaced by a naphthalene, is not an effective inhibitor of a tRNA synthetase [see P. Brown et al. poster presented at the 16th International tRNA Workshop, Madison, Wis., May 27 to Jun. 1, 1995].

Novel synthetic compounds which target tRNA synthetases offer clear advantages as useful therapeutic agents to curb the threat of drug resistance. Drug resistance allows a pathogen to circumvent the biochemical disruption caused by an antimicrobial agent. This resistance can be a result of a mutation that has been selected for and maintained. Pathogens in the environment have had repeated exposure to current therapeutics. This exposure has led to the selection of variant antimicrobial strains resistant to these drugs. Novel synthetic antimicrobial agents, therefore, would be expected to be useful to treat drug resistant pathogens, since the pathogen has never been exposed to the novel antimicrobial agent. The development of compounds or combinations of compounds targeting more than one tRNA synthetase is also advantageous. Accordingly, inhibition of more than one enzyme should reduce the incidence of resistance since multiple mutations in a pathogen would be required and are statistically rare.

SUMMARY OF THE INVENTION

The present invention relates to novel aminoacyl adenylate mimics which inhibit isoleucyl-tRNA synthetases and have efficacy, including whole cell activity, against a broad spectrum of bacteria, fungi and parasites. Described herein are thirty one compounds which exhibit isoleucyl-tRNA synthetase inhibition.

The present invention comprises, in a first aspect, compounds of Formula I

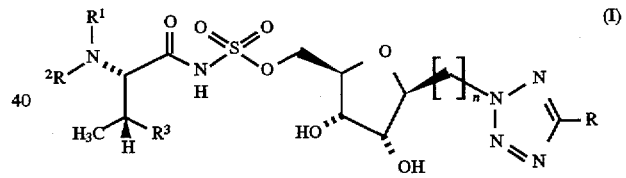

wherein substituent R is selected from amino, alkyl, aryl, cycloalkyl, alkoxy, and aryloxy groups.

Each of substituents $R^1$ and $R^2$ is independently selected from hydrido, alkyl, aryl, carboalkoxy, alkylthiocarbonyl, carboxyamido, and acyl groups.

The substituent $R^3$ of Formula I is selected from ethyl and methoxy groups.

The group n of Formula I is the number 1 or 2.

Preferably, R is alkyl, aryl or cycloalkyl, more preferably, aryl, even more preferably phenyl, substituted phenyl, 5-nitrofuryl or 5-nitrothienyl groups, most preferably p-substituted phenyl. Preferably each of $R^1$ and $R^2$ is independently hydrido or acyl, most preferably hydrido. Preferably $R^3$ is ethyl and n is 2. In preferred forms of this aspect of the invention, any one or more groups from which the substituents R, $R^1$, $R^2$, and $R^3$ are selected can be omitted, provided that said lists each include at least one such group. Pharmaceutically-acceptable salts of compounds of Formula I are also covered by this invention.

A second aspect of the invention comprises using a composition comprising the compound(s) of Formula I to inhibit an isoleucyl-tRNA synthetase and in particular, to modulate the growth of bacterial, fungal or parasitic organisms in mammals.

Further aspects of the invention include intermediates 8 and 19, useful, for example, for formulating compounds of Formula I (vida infra).

DETAILED DESCRIPTION OF THE INVENTION

I. Definitions

Molecular terms, when used in this application, have their common meaning unless otherwise specified. The term "hydrido" denotes a single hydrogen atom. The term "amino" denotes a nitrogen atom containing two substituents independently selected from hydrido, alkyl, cycloalkyl, aryl, acyl, carboxyamido or carboalkoxy groups, wherein the substituent can be the same or different. The term "carboalkoxy" denotes a carbonyl radical adjacent to an alkoxy or aryloxy group. The term "carboxyamido" denotes a carbonyl radical adjacent to an amino group. The term "thio" denotes a divalent sulfur atom containing a substituent selected from hydrido, alkyl, cycloalkyl, or aryl group, such as, methylthio and phenylthio. The term "acyl" denotes a carbonyl radical attached to a hydrido, aryl or alkyl group.

Alkyl groups can be linear or branched, saturated or unsaturated, and have up to about ten carbon atoms. Preferred alkyl groups are "lower alkyl" groups having one to about five carbon atoms. One or more hydrogen atoms can also be replaced by a substitutent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. Examples of alkyl groups include methyl, tert-butyl, isopropyl, propenyl, butadienyl, propynyl, phenylethynyl, (5-nitro-2-furyl)ethynyl, (5-nitro-2-thienyl)-ethynyl, methoxymethyl and benzyl groups. Preferred alkyl groups include substituted alkynyl, dibromoethenyl, benzyl, methyl, trifluoromethyl, 3-phenoxypropyl, and phenoxyphenylmethyl. A more preferred class of alkyl groups are alkynyl groups in which a hydrogen atom is replaced by an aryl group.

Aryl groups can contain zero to four hetero atoms selected from oxygen, nitrogen and sulfur in a single or fused carbocyclic or heterocyclic ring system, having from five to fifteen ring members. One or more hydrogen atoms may also be replaced by a substituent group selected from acyl, amino, carboalkoxy, carboxy, carboxyamido, cyano, halo, hydroxy, nitro, thio, alkyl, aryl, cycloalkyl, alkoxy, aryloxy, sulfoxy, and guanido groups. A preferred class of aryl groups includes unsubstituted phenyl groups, phenyl groups in which one or more hydrogen atoms have been replaced with an alkyl, alkoxy or aryloxy group, 5-nitrofuryl and 5-nitrothienyl groups. Examples of aryl groups include phenyl, naphthyl, biphenyl, terphenyl, pyridinyl, thiazolyl, thiadiazoyl, isoquinolinyl, pyrazolyl, benzothienyl, [(5-nitro-2-thienyl)ethynyl]phenyl, [(5-nitro-2-furyl)ethynyl]phenyl,(phenylalkynyl)phenyl, phenoxyphenyl, [1-(4-carboxymethylphenyl)-phenoxy]phenyl, (4-phenoxyphenoxy)phenyl and pyrrolyl groups.

Cycloalkyl groups have, preferably, saturated or partially unsaturated ring systems, each containing zero to four hetero atoms selected from oxygen, nitrogen and sulfur in a single or fused carbocyclic or heterocyclic ring system having from three to fifteen ring members. One or more hydrogen atoms may also be replaced by a substituent group selected from acyl, amino, carboalkoxy, carboxy, carboxyamido, cyano, halo, hydroxy, nitro, oxo, thio, alkyl, aryl, cycloalkyl, alkoxy, aryloxy, and guanido groups or two substituents together may form a fused cycloalkyl ring. Examples of a cycloalkyl group include cyclopropyl, cyclobutyl, cyclohexyl, cycloheptyl, morpholinyl, piperidinyl, and pyrrolidinyl. An alkoxy group denotes an oxygen atom substituted with an acyl, alkyl or cycloalkyl group. Examples include methoxy, tert-butoxy, benzyloxy, and cyclohexyloxy. An aryloxy group denotes an oxygen atom substituted with an aryl group. Examples of aryloxy groups are phenoxy, 4-carbobenzyloxyphenoxy, 4-phenoxyphenoxy. Preferred aryloxy groups are phenoxy and substituted phenoxy groups. Sulfoxy groups comprise a hexavalent sulfur atom bound to two or three substituents selected from the group consisting of oxo, alkyl, aryl and cycloalkyl groups, wherein at least one of said substituents is oxo.

The pharmaceutically-acceptable salts of the compounds of Formula I include acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of Formula I may be prepared from an inorganic acid or an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of Formula I include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine and procaine. All of these salts may be prepared by conventional means from the corresponding compound of Formula I by treating, for example, the compound of Formula I with the appropriate acid or base.

The compounds of Formula I have centers of asymmetry as indicated by the wedge-shaped and dashed lines. Bonds that extend above the plane of the paper (β bonds) are depicted by darkened wedge-shaped lines, whereas, bonds extending below the plane of the paper are shown as dashed lines. The absolute configuration of these centers is indicated by the stereochemical descriptors R and S, this R and S notation corresponding to the rules described in *Pure Appl. Chem.*, 45, 11–30, (1976). The compounds of this invention may have chiral centers in addition to those indicated. Unless otherwise indicated, the chemical designation of compounds denotes the mixture of all possible stereochemical isomeric forms.

The compounds of Formula I are thus capable of existing in the form of optical isomers as well as in the form of racemic or non-racemic mixtures thereof. The compounds of Formula I can be utilized in the present invention as a single diastereomer or as a mixture of stereochemical isomeric forms. Diastereoisomers can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of Formula I can likewise be obtained by utilizing optically active starting materials. These isomers may be in the form of a free acid, a free base, an ester or a salt.

The invention also embraces isolated compounds. An isolated compound refers to a compound which represents at least 10% of the compound present in the mixture and exhibits a detectable (i.e. statistically significant) antimicrobial or antiparasitic activity when tested in conventional biological assays such as those described herein.

II. Description

According to one aspect of the invention, compounds of Formula I are provided. The compounds are useful for inhibiting the enzymatic activity of an isoleucyl-tRNA synthetase in vivo or in vitro. The compounds are particularly useful as antimicrobial agents and antiparasitic agents, i. e., agents which inhibit the growth of bacteria or fungii and parasites, respectively.

A preferred class of compounds of Formula I are compounds in which R is aryl. Exemplary aryl groups are provided in the definitions.

A further preferred class of compounds of Formula I are compounds in which n is 2 and R is aryl.

A more preferred class of compounds of Formula I are compounds in which n is 2, R is aryl; each of $R^1$ and $R^2$ is hydrido; and $R^3$ is ethyl.

A family of more highly preferred compounds within Formula I consists of compounds of Formula II

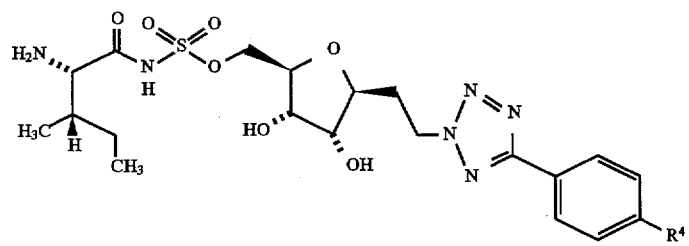

(II)

wherein $R^4$ is selected from alkyl, alkoxy or aryloxy.

An even more preferred family of compounds within Formula II consists of compounds wherein $R^4$ is selected from alkynyl, alkoxy or aryloxy groups substituted with at least one aryl substituent.

Specific compounds most preferred within Formula II are [S-(R*,R*)]-3,6-anhydro-1,2-dideoxy-1-[5-[4-[(5-nitro-2-furyl)ethynyl]phenyl]-2H-tetrazol-2-yl]-D-allo-hepitol 7-(2-amino-3-methyl-1-oxopentyl)sulfamate, [S-(R*,R*)]-3,6-anhydro-1,2-dideoxy-1-[5-[4-[(5-nitro-2-thienyl)ethynyl]phenyl]-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-[4-(4-phenylethynylphenyl)-2H-tetrazol-2-yl]-D-allo-heptitol 7-(2-amino-3-methyl-1-oxopentyl)-sulfamate, [S-(R*,R*)]-3,6-anhydro-1,2-dideoxy-1-[5-(4-phenoxyphenyl)-2H-tetrazol-2-yl]-D-allo-heptitol 7-(2-amino-3-methyl-1-oxopentyl)sulfamate, [S-(R*,R*)]-3,6-anhydro-1,2-dideoxy- 1-[5-[4-(4-phenoxyphenoxy)phenyl]-2H-tetrazol-2-yl]-D-allo-heptitol 7-(2-amino-3-methyl-1-oxopentyl)sulfamate, and [S-(R*,R*)]-3,6-anhydro-1,2-dideoxy-1-[5-[4-(4-carboxymethylphenylphenoxy]phenyl)-2H-tetrazol-2-yl]-D-allo-heptitol 7-(2-amino-3-methyl- 1-oxopentyl) sulfamate, of which [S-(R*,R*)]-3,6-anhydro-1,2-dideoxy-1-[5-[4-[(5-nitro-2-thienyl)ethynyl]phenyl]-2H-tetrazol-2-yl]-D-allo-heptitol 7-(2-amino-3-methyl-1-oxopentyl) sulfamate is especially preferred.

The compounds of the invention are active against a variety of bacterial organisms. They are active against both Gram positive and Gram negative aerobic and anaerobic bacteria, including Staphylococci, for example S. aureus; Enterococci, for example E. faecalis; Streptococci, for example S. pneumoniae; Haemophilus, for example H. influenza; Moraxella, for example M. catarrhalis; and Escherichia, for example E. coli. The compounds of the present invention are also active against Mycobacteria, for example M. tuberculosis. The compounds of the present invention are also active against intercellular microbes, for example Chlamydia and Rickettsiae. The compounds of the present invention are also active against Mycoplasma, for example M. pneumoniae.

The compounds of the present invention are also active against fungal organisms, including, among other organisms, the species Aspergillus, Blastomyces, Candida, Coccidioides, Cryptococcus, Epidermophyton, Hendersonula, Histoplasma, Microsporum, Paecilomyces, Paracoccidioides, Pneumocystis, Trichophyton, and Trichosporium.

The compounds of the present invention are also active against parasites, including Protozoa and Helminths. Examples of such parasitic species include, among others, Entamoeba, Leishmania, Toxoplasma, Trichinosis, and Schistosomiasis.

The phrase "therapeutically-effective amount" means that amount of a compound of Formula I which prevents the onset of, alleviates the symptoms of, or stops the progression of an infection (e. g. a microbial or parasitic infection) in vivo or in vitro. The term "microbial" means bacterial and fungal, for example a "microbial infection" means a bacterial or fungal infection. The term "treating" is defined as administering, to a subject, a therapeutically-effective amount of a compound of Formula I. The term "subject", as described herein, is defined as a mammal, a plant or a cell culture.

In a second aspect, the invention provides a pharmaceutical composition comprising a compound of the invention, preferably a compound in accordance with the first aspect of the invention, and a pharmaceutically-acceptable carrier.

According to another aspect of the invention, a method for inhibiting an isoleucyl-tRNA synthetase is provided which comprises contacting an isoleucyl-tRNA synthetase with a compound of Formula I under the conditions in which the isoleucyl-tRNA synthetase interacts with it's substrate to form an aminoacyl adenylate intermediate and, preferably to further form a charged tRNA. Such conditions are known to those skilled in the art (see also e.g., the Examples for conditions). This method involves contacting an isoleucyl-tRNA synthetase with an amount of compound of Formula I that is sufficient to result in detectable isoleucyl-tRNA synthetase inhibition. This method can be performed on an isoleucyl-tRNA synthetase that is contained within an organism or outside an organism. In a further aspect, the invention provides a method for inhibiting the growth of microorganisms, preferably bacteria or fungi, comprising contacting said organisms with a compound of the invention (preferably a compound of Formula I) under conditions which permit entry of the compound into said organism. Such conditions are known to one skilled in the art and are examplified in the Examples. This method involves contacting a microbial or parasitic cell with a therapeutically-effective amount of a compound(s) of Formula I, e.g. to inhibit cellular isoleucyl-tRNA synthetase in vivo or in vitro. This method is used in vivo, for example, for treating microbial or parasitic infections in mammals. Alternatively, the method is used in vitro, for example, to eliminate microbial or parasitic contaminants in a cell culture, or in a plant.

In accordance with another aspect of the invention, the compositions disclosed herein are used for treating a subject afflicted by or susceptible to a microbial or parasitic infection. The method involves administering to the subject a therapeutically-effective amount of the compound of Formula I. According to this aspect of the invention, the novel compositions disclosed herein are placed in a pharmaceutically-acceptable carrier and are delivered to a recipient subject (preferably a human) in accordance with known methods of drug delivery. Exemplary procedures for delivering an antibacterial, antifungal and antimycoplasmal agent are described in U.S. Pat. No. 5,041,567, issued to Rogers et al. and in PCT patent application number EP94/02552 (publication no. WO 95/05384), the entire contents of which documents are incorporated in their entirety herein by reference. In general, the methods of the invention for delivering the compositions of Formula I in vivo utilize art-recognized protocols for delivering the agent with the only substantial procedural modification being the substitution of the compounds of Formula I for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of Formula I for the agents used in the art-recognized protocols.

The pharmaceutical preparations disclosed herein are prepared in accordance with standard procedures and are administered at dosages that are selected to reduce, prevent or eliminate the infection (See, e.g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antimicrobial agents for human therapy). The compositions of Formula I can be delivered using controlled or sustained release delivery systems (e.g., capsules, bioerodable matrices). Exemplary delayed release delivery systems for drug delivery that would be suitable for administration of the compositions of Formula I are described in U.S. Pat. No. 4,452,775 (issued to Kent), U.S. Pat. No. 5,039,660 (issued to Leonard), U.S. Pat. No. 3,854,480 (issued to Zaffaroni).

The pharmaceutically-acceptable compositions of the present invention comprise one or more compounds of Formula I in association with one or more nontoxic, pharmaceutically-acceptable carriers and/or diluents and/or adjuvants and/or excipients, collectively referred to herein as "carrier" materials, and if desired other active ingredients.

The compounds of the present invention may be administered by any route, preferably in the form of a pharmaceutical composition adapted to such a route, and would be dependent on the condition being treated. The compounds and compositions may, for example, be administered orally, intravascularly, intraperitoneally, subcutaneously, intramuscularly or topically.

For oral administration, the pharmaceutical compositions may be in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

The pharmaceutical compositions may also be administered via injection. Formulations for parenteral administration may be in the form of aqueous or non-aqueous isotonic sterile injection solutions or suspensions. These solutions or suspensions may be prepared from sterile powders or granules having one or more of the carriers mentioned for use in the formulations for oral administration. The compounds may be dissolved in polyethylene glycol, propylene glycol, ethanol, corn oil, benzyl alcohol, sodium chloride, and/or various buffers.

For topical use the compounds of the present invention may also be prepared in suitable forms to be applied to the skin, or mucus membranes of the nose and throat, and may take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention may be presented in liquid or semi-liquid form formulated in hydrophobic or hydrophilic bases as ointments, creams, lotions, paints or powders.

For rectal administration the compounds of the present invention may be administered in the form of suppositories admixed with conventional carriers such as cocoa butter, wax or other glyceride.

Alternatively, the compounds of the present invention may be in powder form for reconstitution at the time of delivery.

The dosage regimen for treating an infection with the compound and/or compositions of this invention is selected in accordance with a variety of factors, including the type, age, weight, sex and medical condition of the patient, the severity of the infection, the route and frequency of administration and the particular compound employed. In general, dosages are determined in accordance with standard practice for optimizing the correct dosage for treating an infection.

The compositions may contain from 0.1% to 99% by weight, preferably 10–60% by weight, of the active ingredient, depending on the method of administration. If the compositions contain dosage units, each dosage unit will preferably contain from 50–500 mg of the active material. For adult human treatment, the dosage employed will preferably range from 100 mg to 3 g, per day, depending on the route and frequency of administration.

If administered as part of a total dietary intake, the amount of compound employed may be less than 1% by weight of the diet and preferably no more than 0.5% by weight. The diet for animals may be normal foodstuffs to which the compound may be added or it may be added to a premix.

Further references to features and aspects of the invention are provided in the Claims and Examples set out hereafter.

GENERAL SYNTHETIC PROCEDURES

General Procedure 1

Compound 1, prepared from commercial D-Ribose via the procedure disclosed in H. Ohrui et al., *J. Am. Chem. Soc.*, 97(16), 4602–4613, (1975), is converted to compound 2 by treatment with reagent A and a base such as imidazole or potassium carbonate in an appropriate solvent such as tetrahydrofuran, dichloromethane, dimethyl sulfoxide or dimethylformamide at temperatures ranging from 0° C. to 75° C. In the reactions which follow, each of the intermediates is optionally purified via the purification methods described in the specific examples.

Reaction 1

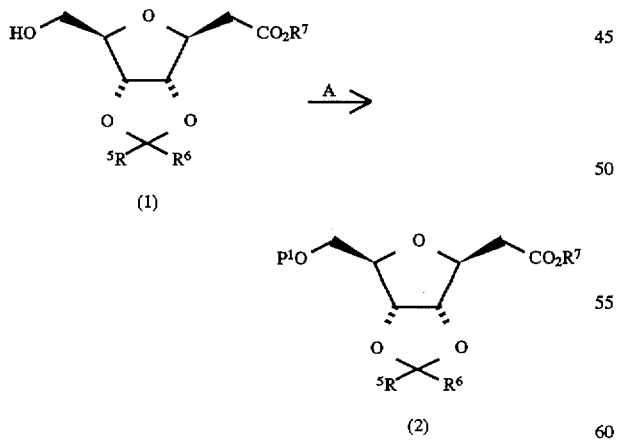

wherein each of $R^5$ and $R^6$ is independently selected from hydrido, alkyl, aryl, or cycloalkyl; wherein $R^7$ is selected from alkyl, cycloalkyl or aryl; wherein A is an alcohol protecting reagent such as benzyl bromide, chlorotrimethylsilane, tert-butyldimethylsilyl chloride or chloromethyl methyl ether; wherein $P^1$ is a protecting group selected from alkoxymethyl, aryloxymethyl, thiomethyl, arylmethyl, trialkylsilyl, triarylsilyl, diphenylmethylsilyl, diphenyl-tert-butylsilyl, (phenyldimethylsilyl)methoxymethyl, 2-(trimethylsilyl)ethoxymethyl, or tetrahydropyranyl, for example, benzyl, trimethylsilyl, tert-butyldimethylsilyl and methoxymethyl. In preferred forms of this aspect of the invention, any one or more groups from which the substituent $P^1$ is selected can be omitted, provided that said list includes at least one such group.

Compound 2 is converted to compound 3 by treatment with B in an appropriate solvent such as toluene, dichloromethane, tetrahydrofuran, methanol, ethanol, or 2-methoxyethyl ether, at temperatures ranging from −78° C. to 100° C.

Reaction 2

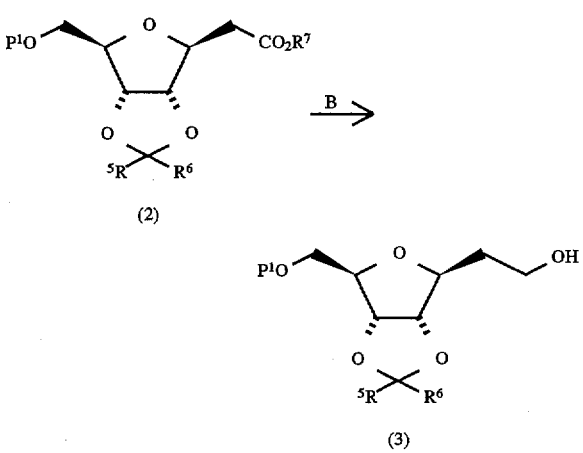

wherein $R^5$, $R^6$, $R^7$ and $P^1$ are as previously described; wherein B is a reducing agent such as lithium aluminum hydride, aluminum hydride, lithium borohydride, or diisobutylaluminum hydride.

Compound 3 is converted to compound 4 by treatment with C and a base such as imidazole or potassium carbonate in an appropriate solvent such as tetrahydrofuran, diethyl ether, dimethyl sulfoxide or dimethylformamide at temperatures ranging from 0° C. to 75° C.

Reaction 3

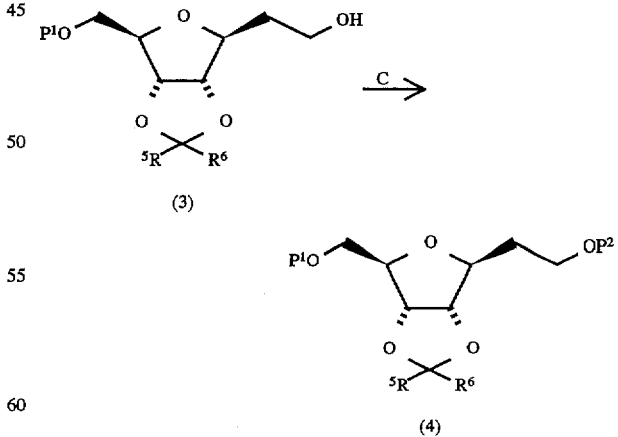

wherein $R^5$, $R^6$ and $P^1$ are as previously described; wherein C is an alcohol protecting reagent such as benzyl bromide, chlorotrimethylsilane, tert-butyldimethylsilyl chloride, chloromethyl methyl ether or benzoyl chloride such that A is not the same as C; wherein $P^2$ is a protecting group selected from acyl, alkoxymethyl, aryloxymethyl, thiomethyl, arylmethyl, trialkylsilyl, triarylsilyl, diphenylmethylsilyl, diphenyl-tert-butylsilyl, (phenyldimethylsilyl)methoxymethyl, 2-(trimethylsilyl)ethoxymethyl, or tetrahydropyranyl, for example, benzyl, trimethylsilyl, tert-butyldimethylsilyl and methoxymethyl; wherein A and C are chosen such that either group $P^1$ or $P^2$ can be removed without removing the other. In preferred forms of this aspect of the invention, any one or more groups from which the substituent $P^2$ is selected can be omitted, provided that said list includes at least one such group.

Compound 4 is converted to compound 5 by treatment with D in an appropriate solvent such as tetrahydrofuran, dichloromethane or diethyl ether at temperatures ranging from 0° C. to 40° C.

Reaction 4

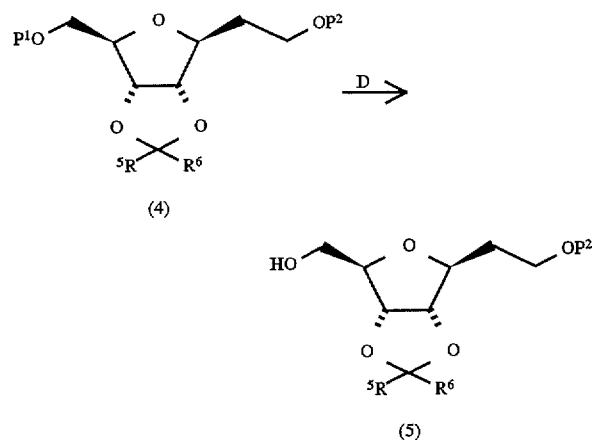

wherein $R^5$, $R^6$, $P^1$ and $P^2$ are as previously described; wherein D is an alcohol deprotecting reagent capable of removing $P^1$ without removing $P^2$, such as tetrabutylammonium fluoride, HF-pyridine, 2,3-dichloro-5,6-dicyano-1,4-benzoquinone, sodium methoxide, lithium hydroxide or hydrogen gas in the presence of a catalyst such as palladium-on-carbon, platinum oxide or palladium chloride.

Compound 5 is converted to compound 7 by treatment with compound 6 and a base such as triethylamine, 4-methylmorpholine or diisopropylethylamine in an appropriate solvent such as dichloromethane or toluene at temperatures ranging from −20° C. to 40° C.

Reaction 5

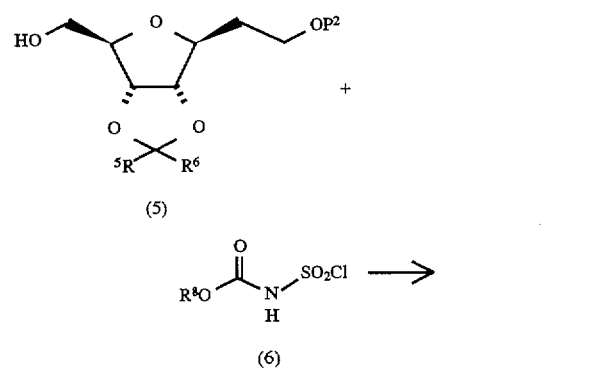

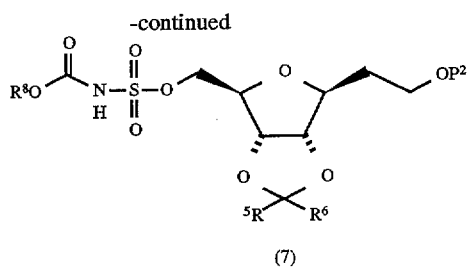

wherein $R^5$, $R^6$ and $P^2$ are as previously defined; wherein $R^8$ is alkyl.

Compound 7 is converted to compound 8 by treatment with E and gaseous hydrogen at 1 to 4 atmospheres in an appropriate solvent such as ethyl acetate, methanol or ethanol at temperatures ranging from ambient to 50° C.

Reaction 6

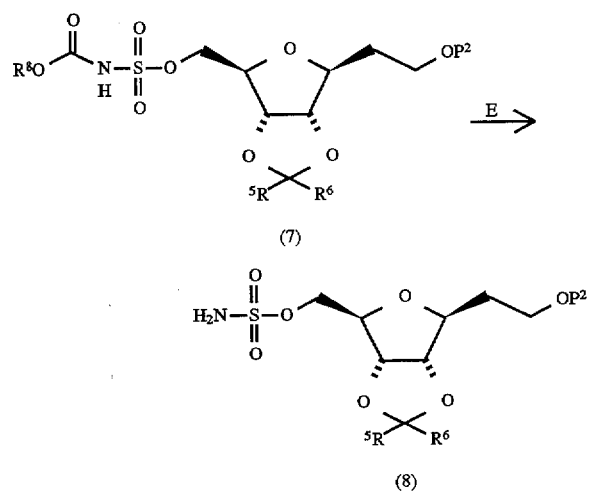

wherein $R^5$, $R^6$, $R^8$, and $P^2$ are as previously defined; wherein E is a catalyst such as palladium-on-carbon, platinum oxide or palladium chloride.

Compound 8 is converted to compound 10 by treatment with compound 9, F and G in an appropriate solvent such as dichloromethane or dimethylformamide at temperatures ranging from −25° C. to ambient.

Reaction 7

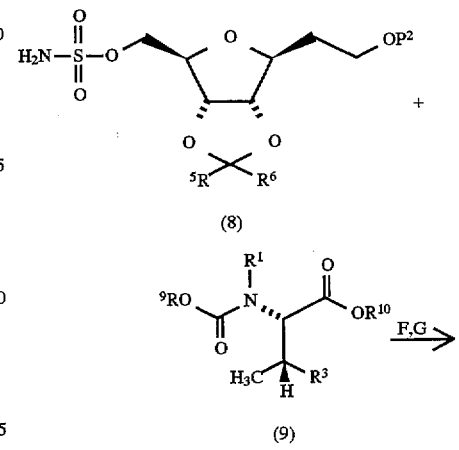

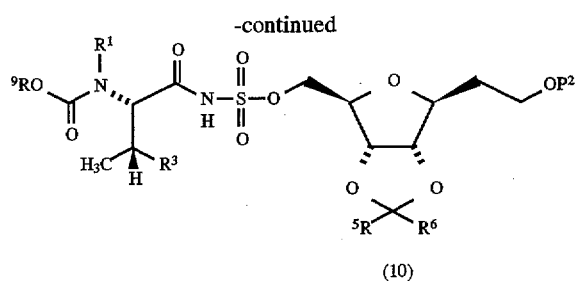

(10)

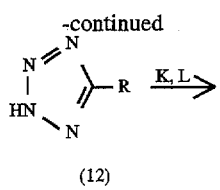

(12)

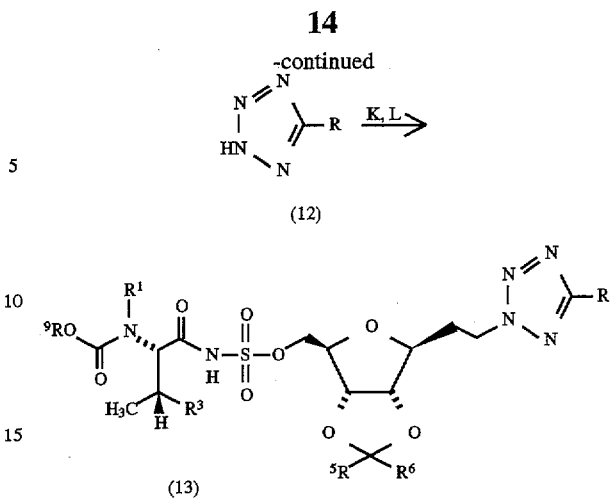

(13)

wherein $R^1$, $R^3$, $R^5$, $R^6$, and $P^2$ are as previously defined; wherein $R^9$ is selected from aryl, alkyl or cycloalkyl; wherein $R^{10}$ is selected from hydrido, aryl, succinimidyl or benzotriazolyl; wherein F is a dehydrating agent such as dicyclohexylcarbodiimide or ethyl-3-(3-dimethylaminopropyl)carbodiimide; wherein G is an acylation catalyst such as 4-dimethylaminopyridine.

Compound 10 is converted to compound 11 by treatment with J in an appropriate solvent such as methanol, tetrahydrofuran, dichloromethane, or water at temperatures ranging from −25° C. to 40° C.

Reaction 8

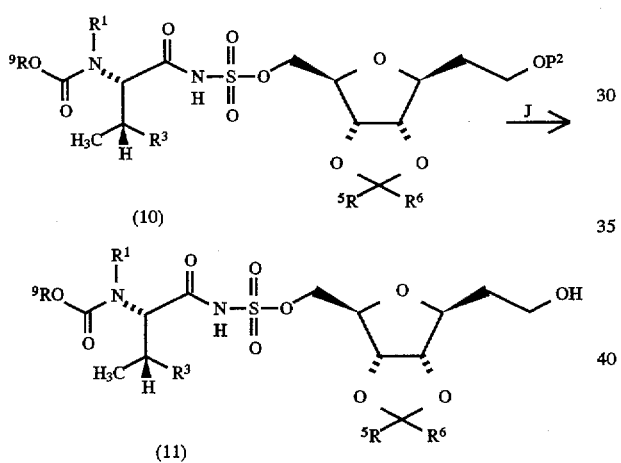

wherein $R^1$, $R^3$, $R^5$, $R^6$, $R^9$, and $P^2$ are as previously defined; wherein J is a reagent capable of removing the protecting group $P^2$ such as sodium hydroxide, sodium methoxide, tetrabutylammonium fluoride, HF-pyridine or 2,3-dichloro-5,6-dicyano-1,4-benzoquinone.

Compound 11 is converted to compound 13 by treatment with compound 12, K and L in an appropriate solvent such as dichloromethane or tetrahydrofuran at temperatures ranging from −25° C. to ambient.

Reaction 9

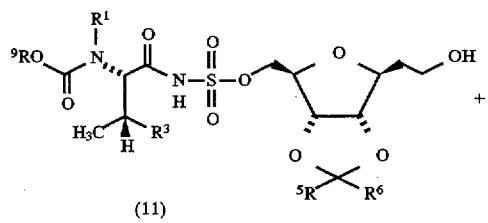

wherein R, $R^1$, $R^3$, $R^5$, $R^6$, and $R^9$ are as previously defined; wherein K is a trialkylphosphine, or triarylphosphine such as triphenylphosphine; wherein L is a dialkylazodicarboxylate such as diethylazodicarboxylate or diisopropylazodicarboxylate.

Compounds of Formula I are obtained by partial or full deprotection of compound 13 according to standard procedures known to those skilled in the art (See e.g. Protective Groups in Organic Chemistry, 2nd Edition, T. W. Greene, P. G. M. Wuts, Wiley Interscience, New York, 1991, the contents of which are incorporated by reference, for a general description of the methods for deprotecting protecting groups). Typically compound 13 is treated in one of the three following ways:

1) Compound 13 is treated with trifluoroacetic acid and water (5:2) at temperatures ranging from 0° C. to 70° C. or, 2) Compound 13 is treated as described in step 1 above then treated with E (vide supra) and hydrogen gas at 1 to 4 atmospheres in an appropriate solvent such as ethyl acetate, methanol or ethanol at temperatures ranging from ambient to 50° C., or 3) Compound 13 is first treated with E as described in step 2 above then treated as per step 1 above.

General Procedure 2

Compound 14 [For preparation see K. Utimoto et al., Tetrahedron Lett. 23(2), 237–8, (1982)] is converted to compound 15 by treatment with a base such as sodium methoxide, lithium hydroxide or sodium ethoxide followed by an acid such as hydrochloric acid, sulfuric acid or Amberlite® IR120(H+) resin (Rohm and Haas Company, Philadelphia, Pa.) in an appropriate solvent such as methanol, ethanol, tetrahydrofuran or toluene at temperatures ranging from 0° C. to 75° C.

Reaction 10

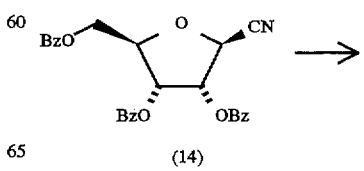

(14)

-continued

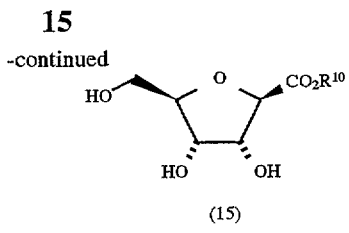

(15)

wherein $R^{10}$ is alkyl.

Compound 15 is converted to compound 16 by treatment with M in the presence of an acid such as sulfuric acid, phosphoric acid, 4-toluenesulfonic acid, camphorsulfonic acid, or copper(II)sulfate in an appropriate solvent such as acetone, diethyl ether or toluene at temperatures ranging from 0° C. to the boiling point of the solvent.

Reaction 11

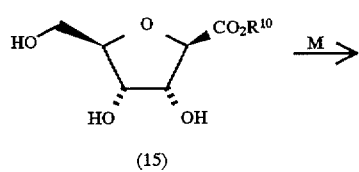

(15)

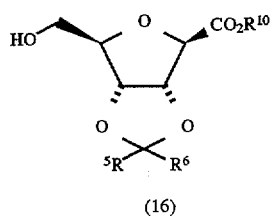

(16)

wherein $R^5$, $R^6$ and $R^{10}$ are as previously defined; wherein M is an aldehyde, ketone or their synthetic equivalents such as 2,2-dimethoxypropane or 2-methoxypropene.

Compound 16 is converted to compound 17 by treatment with A according to Reaction 1 of General Procedure 1.

Reaction 12

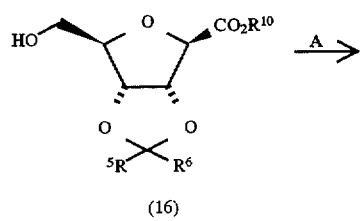

(16)

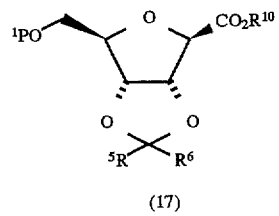

(17)

wherein $R^5$, $R^6$, $R^{10}$, $P^1$ and A are as previously defined.

Compound 17 is converted to compound 18 by treatment with B according to Reaction 2 of General Procedure 1.

Reaction 13

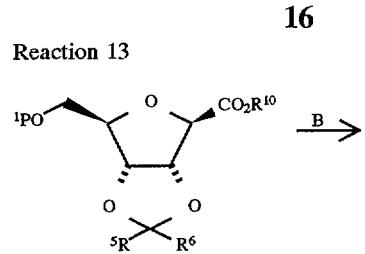

(17)

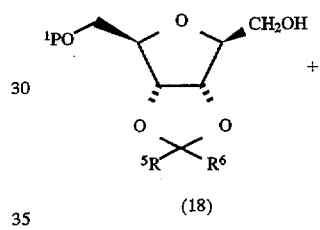

(18)

wherein $R^5$, $R^6$, $R^{10}$, $P^1$, and B are as previously described.

Compound 18 is converted to compound 19 by treatment with compound 12, K and L according to Reaction 9 of General Procedure 1.

Reaction 14

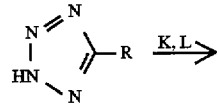

(18)

+

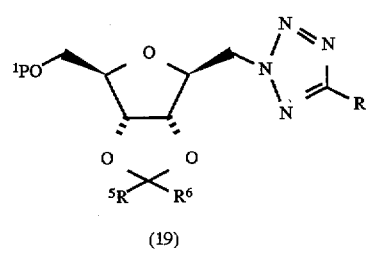

(12)

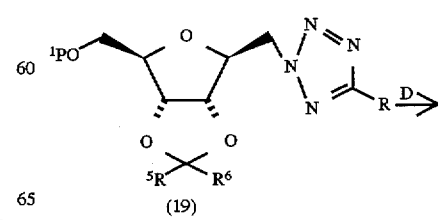

(19)

wherein R, $R^5$, $R^6$, $P^1$, K and L are as previously defined.

Compound 19 is converted to compound 20 by treatment with D according to Reaction 4 of General Procedure 1.

Reaction 15

(19)

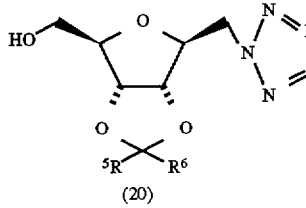

(20)

wherein R, $R^5$, $R^6$, $P^1$ and D are as previously defined.

Compound 20 is converted to compound 21 by treatment with compound 6 according to Reaction 5 of General Procedure 1.

Reaction 16

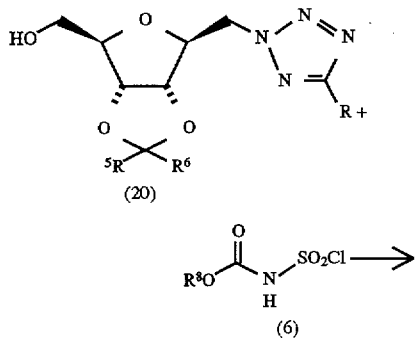

wherein R, $R^5$, $R^6$ and $R^8$ are as previously defined.

Compound 21 is converted to compound 22 by treatment with E according to Reaction 6 of General Procedure 1.

Reaction 17

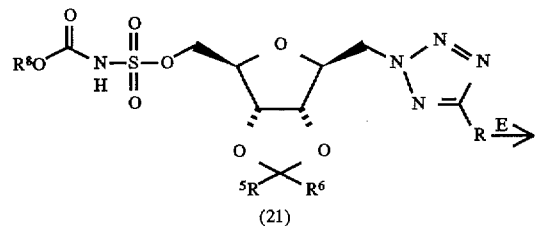

wherein R, $R^5$, $R^6$, $R^8$ and E are as previously defined.

Compound 22 is converted to compound 23 by treatment with compound 9, F and G according to Reaction 7 of General Procedure 1.

Reaction 18

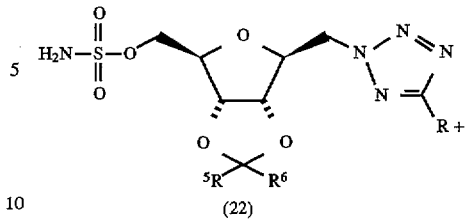

(22)

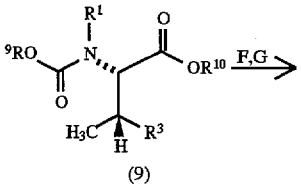

(9)

(23)

wherein R, $R^1$, $R^3$, $R^5$, $R^6$, $R^9$, $R^{10}$, F and G are as previously defined.

Compound 23 may be partially or fully deprotected according to the standard procedures that apply to compound 13 in General Procedure 1.

The preparation of representative compounds of Formula I is described in detail in Example Procedures 1–4, below. Table I is a list of specific examples within Formula I.

EXAMPLES

The following Examples 1–4 are detailed descriptions of the methods of preparation of compounds of Formula I. These detailed preparations fall within the scope of, and serve to exemplify, the above described General Procedures which form part of the invention. These Examples 1–4 are presented for illustrative purposes only and are not intended as a limitation on the scope of the invention.

Example 1

Preparation of [S-(R*,R*)]-3,6-anhydro- 1,2-dideoxy-1-[5-(4-phenoxyphenyl)-2H-tetrazol-2-yl]-D-allo-heptitol 7-(2-amino-3-methyl-1-oxopentyl) sulfamate.

To a solution of 3,6-anhydro-2-deoxy-4,5-O-(1-methylethylidene)-D-allo-heptonoic acid methyl ester (116 g, see H. Ohrui et al., *J. Am. Chem. Soc.*, 97 (16), 4602–4613 (1975)) in anhydrous tetrahydrofuran (1 L) was added imidazole (47.9 g) and tert-butyldimethylsilyl chloride (85.2 g). The mixture was stirred at room temperature for 2 hours, filtered and evaporated to dryness. The residue was dissolved in diethyl ether (500 ml), chilled to 0° C. and filtered again. The filtrate was then washed with 1M hydrochloric acid (2×100 ml), dried over anhydrous sodium sulfate, filtered and evaporated to dryness to give 3,6-anhydro-2-deoxy-7-O-[(1,1-dimethylethyl)dimethylsilyl]-4,5-O-(1-methylethylidene)-D-allo-heptonoic acid methyl ester as a colorless oil.

To a 0° C. suspension of lithium aluminum hydride (1.34 g) in anhydrous tetrahydrofuran (100 ml) was added 3,6-anhydro-2-deoxy-7-O-[(1,1-dimethylethyl)dimethylsilyl]-4,5-O-(1-methylethylidene)-D-allo-heptonoic acid methyl ester (12.0 g) in anhydrous tetrahydrofuran (100 ml) dropwise over 30 minutes. The reaction mixture was then quenched by dropwise addition of water (1.5 ml) followed by dropwise addition of 15% sodium hydroxide (1.5 ml) and water (4.5 ml). Anhydrous sodium sulfate was added to the mixture which was then filtered through Celite® (diatomaceous earth, Johns-Manville, New York, N.Y.), and evaporated to dryness to yield 3,6-anhydro-2-deoxy-7-O-[(1,1-dimethylethyl)dimethylsilyl]-4,5-O-(1-methylethylidene)-D-allo-heptitol as a clear oil.

To a stirred 0° C. solution of 3,6-anhydro-2-deoxy-7-O-[(1,1-dimethylethyl) dimethylsilyl]-4,5-O-(1-methylethylidene)-D-allo-heptitol (20.0 g), triethylamine (20 ml) and 4-dimethylaminopyridine (0.35 g) in anhydrous dichloromethane (300 ml) was slowly added benzoyl chloride (7.5 ml). After 1 hour, saturated sodium bicarbonate (200 ml) was added. After an additional hour the organic layer was washed with saturated sodium bicarbonate (100 ml) and 1M hydrochloric acid (100 ml). The organic layer was then dried over anhydrous magnesium sulfate, filtered and evaporated to dryness to yield 3,6-anhydro-1-O-benzoyl-2-deoxy-7-O-[(1,1-dimethylethyl)dimethylsilyl]-4,5-O-(1-methylethylidene)-D-allo-heptitol as a clear oil.

3,6-anhydro-1-O-benzoyl-2-deoxy-7-O-[(1,1-dimethylethyl)dimethylsilyl]-4,5-O-(1-methylethylidene)-D-allo-heptitol (100.6 g) was dissolved in tetrahydrofuran (750 ml) and treated with 2.73M aqueous tetrabutylammonium fluoride (84.4 ml). The reaction mixture was stirred for 4 hours at room temperature then evaporated to dryness. The residue was dissolved in ethyl acetate (1 L) and washed with water (3×500 ml). The organic layer was dried over anhydrous magnesium sulfate, filtered and evaporated. The residue was purified by silica gel chromatography (20–50% ethyl acetate in hexanes) to give 3,6-anhydro-1-O-benzoyl-2-deoxy-4,5-O-(1-methylethylidene)-D-allo-heptitol as a colorless oil.

To a 0° C. solution of chlorosulfonyl isocyanate (4.7 ml) in anhydrous tetrahydrofuran (250 ml) was added benzyl alcohol (5.6 ml) with vigorous stirring. After 45 minutes the solution was added to a solution of 3,6-anhydro-1-O-benzoyl-2-deoxy-4,5-O-(1-methylethylidene)-D-allo-heptitol (11.6 g) and triethylamine (30 ml) in anhydrous tetrahydrofuran (500 ml) at 0° C. The mixture was allowed to warm to room temperature over 16 hours then phenylmethoxycarbonyl sulfamoyl chloride (4.5 g) was added. After an additional 1 hour the mixture was evaporated to dryness and the residue was dissolved in ethyl acetate (500 ml). The organic solution was washed with 1M hydrochloric acid (2×300 ml), water (200 ml), and saturated sodium chloride (100 ml). The organic layer was dried over anhydrous sodium sulfate, filtered and evaporated to dryness to yield 3,6-anhydro-1-O-benzoyl-2-deoxy-4,5-O-(1-methylethylidene)-D-allo-heptitol 7-[(phenylmethoxy)carbonyl]sulfamate as a tan oil.

To a solution of 3,6-anhydro-1-O-benzoyl-2-deoxy-4,5-O-(1-methylethylidene)-D-allo-heptitol 7-[(phenylmethoxy)carbonyl]sulfamate (141 g) in ethanol (300 ml) was added Raney Nickel® (50 g, nickel-aluminum alloy, W. R. Grace, Boca Raton, Fla.). The mixture was heated to reflux for 1 hour then allowed to cool to room temperature. The cooled mixture was then filtered and evaporated to dryness. The residue was dissolved in methanol (500 ml) and stirred at room temperature under 1 atmosphere of hydrogen with 10% palladium on carbon (4 g) for 1 day. The mixture was filtered through Celite® (diatomaceous earth, Johns-Manville, New York, N.Y.), evaporated and the residue was purified by silica gel chromatography (40% ethyl acetate in hexanes) to give 3,6-anhydro-1-O-benzoyl-2-deoxy-4,5-O-(1-methylethylidene)-D-allo-heptitol 7-sulfamate as a yellow oil.

To a stirred solution of 3,6-anhydro-1-O-benzoyl-2-deoxy-4,5-O-(1-methyl-ethylidene)-D-allo-heptitol 7-sulfamate (11.6 g), N-tert-butoxycarbonyl-2(S),3(S)-isoleucine (10.0 g), triethylamine (11 ml) and 4-dimethylaminopyridine (14.2 g) in anhydrous dichloromethane (100 ml) was added ethyl-3-(3-dimethylamino)propylcarbodiimide hydrochloride (8.3 g). The mixture was stirred for 65 hours at room temperature then diluted with ethyl acetate (500 ml) and washed with 1M hydrochloric acid (2×250 ml), water (2×250 ml), saturated sodium bicarbonate (2×250 ml) and saturated sodium chloride (2×250 ml). The organic layer was dried over anhydrous sodium sulfate, filtered and evaporated to dryness to yield [S-(R*,R*)]-3,6-anhydro-1-O-benzoyl-2-deoxy-4,5-O-(1-methylethylidene)-D-allo-heptitol 7-[2-[(1,1-dimethylethoxy)carbonylamino]-3-methyl-1-oxopentyl]sulfamate as a white foam.

[S-(R*,R*)]-3,6-anhydro-1-O-benzoyl-2-deoxy-4,5-O-(1-methylethylidene)-D-allo-heptitol 7-[2-[(1,1-dimethylethoxy)carbonylamino]-3-methyl-1-oxopentyl]sulfamate (18.9 g) was dissolved in tetrahydrofuran (80 ml), methanol (80 ml), and 1M sodium hydroxide (100 ml). After stirring for 1.5 hours at room temperature, the mixture was diluted with ethyl acetate (500 ml) and the organic layer was washed with saturated sodium sulfate (100 ml). The combined aqueous layer was then washed with ethyl acetate (250 ml). The combined organic layer was dried over anhydrous sodium sulfate, filtered and evaporated to dryness to yield [S-(R*,R*)]-3,6-anhydro-2-deoxy-4,5-O-(1-methylethylidene)-D-allo-heptitol 7-[2-[(1,1-dimethylethoxy)carbonylamino]-3-methyl-1-oxopentyl]sulfamate as a white foam.

A solution of 4-phenoxybenzonitrile (9.87 g), dibutyltin oxide (3.88 g), and trimethylsilyl azide (33.5 ml) in anhydrous toluene (200 ml) was heated to reflux for 6 hours. The reaction mixture was washed with 1.6M sodium hydroxide (2×250 ml). The combined aqueous layer was washed with diethyl ether (4×120 ml) then acidified to pH 6 with concentrated hydrochloric acid. The acidic solution was washed with ethyl acetate (3×200 ml) and the combined organic layer was dried over anhydrous sodium sulfate, filtered and evaporated to dryness to give 5-(4-phenoxyphenyl)-1H-tetrazole as a white powder.

To a room temperature solution of [S-(R*,R*)]-3,6-anhydro-2-deoxy-4,5-O-(1-methylethylidene)-D-allo-heptitol 7-[2-[(1,1-dimethylethoxy)carbonylamino]-3-methyl-1-oxopentyl]sulfamate (306 mg), triphenylphosphine (314 mg) and 5-(4-phenoxyphenyl)-1H-tetrazole (165 mg) in anhydrous tetrahydrofuran (3 ml) was added diisopropylazo-dicarboxylate (242 mg) dropwise. The reaction mixture stirred overnight then concentrated and purified by silica gel chromatography (5% methanol in dichloromethane) to give [S-(R*,R*)]-3,6-anhydro-1,2-dideoxy-4,5-O-(1-methylethylidene)-1-[5-(4-phenoxyphenyl)-2H-tetrazol-2-yl]-D-allo-heptitol 7-[2-[(1,1-dimethylethoxy)carbonylamino]-3-methyl-1-oxopentyl]-sulfamate as a white foam.

[S-(R*,R*)]-3,6-anhydro-1,2-dideoxy-4,5-O-(1-methylethylidene)-1-[5-(4-phenoxyphenyl)-2H-tetrazol-2- yl]-D-allo-heptitol 7-[2-[(1,1-dimethylethoxy)
carbonylamino]-3-methyl-1-oxopentyl]sulfamate (321 mg)
was treated with a solution of trifluoroacetic acid (2.5 ml)
and dichloromethane (2.5 ml) for 2 minutes at room temperature. Five drops of water was added and the solution was stirred an additional 2 hours. The mixture was then evaporated to dryness followed by azeotropic removal of remaining water with toluene (10 ml). The residue was purified by silica gel chromatography (10 % methanol in dichloromethane) to give [S-(R*,R*)]-3,6-anhydro-1,2-dideoxy-1-[5-(4-phenoxyphenyl)-2H-tetrazol-2-yl]-D-allo-heptitol 7-(2-amino-3-methyl-1-oxopentyl)sulfamate as a white solid.

Example 2

Preparation of [S-(R*,R*)]-3,6-anhydro-1,2-
dideoxy-1-[5-[4-[(5-nitro-2-furyl)ethynyl]phenyl]-
2H-tetrazol-2-yl]-D-allo-heptitol 7-(2-amino-3-
methyl-1-oxopentyl)sulfamate To a solution of 2-bromo-5-nitrofuran (1.65 g) and triethylamine (34 ml) in anhydrous acetonitrile (55 ml) under nitrogen was added bis(triphenylphosphine)palladium dichloride (130 mg) and cuprous iodide (35 mg). 4-Ethynylbenzonitrile (1.09 g) was added and the reaction mixture was stirred under nitrogen overnight. The mixture was evaporated to dryness and the residue was dissolved in dichloromethane (200 ml), dried over anhydrous sodium sulfate, filtered and evaporated to dryness. The residue was purified by silica gel chromatography (ethyl acetate/hexane 1:10) and triturated with ethyl acetate/hexane (1:3) to give 4-[(5-nitro-2-furyl)-ethynyl]benzonitrile.

To a solution of 4-[(5-nitro-2-furyl)ethynyl]benzonitrile (0.733 g) and dibutyltin oxide (77 mg) in anhydrous toluene (30 ml) was added trimethylsilyl azide (0.5 ml ). The solution was heated to reflux in the dark for 12 hours. Trimethylsilyl azide (0.5 ml ) was added and the reaction mixture was heated to reflux for an additional 1 day, then allowed to cool to room temperature. The solution was then washed with saturated sodium bicarbonate (2×300 ml). The combined aqueous layer was acidified to pH 1 with concentrated hydrochloric acid (30 ml ) then washed with 1:1 ethyl acetate/tetrahydrofuran (500 ml). The organic layer was dried over anhydrous sodium sulfate, filtered and evaporated to dryness to give 5-[4-[(5-nitro-2-furyl)ethynyl]phenyl]-1H-tetrazole as a yellow solid.

To a solution of [S-(R*,R*)]-3,6-anhydro-2-deoxy-4,5-O-(1-methylethylidene)-D-allo-heptitol 7-[2-[(1,1-dimethylethoxy)carbonylamino]-3-methyl-1-oxopentyl] sulfamate (1.10 g), triphenylphosphine (1.70 g) and 5-[4-[(5-nitro-2-furyl)ethynyl]phenyl]-1H-tetrazole (0.73 g) in anhydrous tetrahydrofuran (40 ml) was added diisopropylazodicarboxylate (0.86 ml). The reaction mixture was stirred at room temperature for 12 hours then diluted with ethyl acetate (200 ml), washed with 1M hydrochloric acid (100 ml), saturated sodium bicarbonate (200 ml), and 1M hydrochloric acid (100 ml). The organic layer was dried over anhydrous sodium sulfate, filtered and evaporated to dryness. The residue was purified by silica gel chromatography (2–4% methanol in dichloromethane) to give [S-(R*,R*)]-3,6-anhydro-1,2-dideoxy-4,5-O-(1-methylethylidene)-1-[5-[4-[(5-nitro-2-furyl)ethynyl]phenyl]-2H-tetrazol-2yl]-D-allo-heptitol 7-[2-[(1,1-dimethylethoxy)-carbonylamino]-3-methyl-1-oxopentyl]sulfamate as a yellow foam.

To a solution of trifluoroacetic acid (7.5 ml) and water (3 ml) was added [S-(R*,R*)]-3,6-anhydro-1,2-dideoxy-4,5-O-(1-methylethylidene)-1-[5-[4-[(5-nitro-2-furyl)ethynyl] phenyl]-2H-tetrazol-2-yl]-D-allo-heptitol 7-[2-[(1,1-dimethylethoxy)-carbonylamino]-3-methyl-1-oxopentyl] sulfamate (0.45 g). The mixture was stirred at room temperature for 1.25 hours then evaporated to dryness. Toluene (15 ml) was added to the solid and the mixture was evaporated to dryness. The residue was recrystallized from 1:2 tetrahydrofuran/diethyl ether (15 ml) to give [S-(R*,R*)]-3,6-anhydro-1,2-dideoxy-1-[5-[4-[(5-nitro-2-furyl) ethynylphenyl]-2-tetrazol-2-yl]-D-allo-heptitol 7-(2-amino-3-methyl-1-oxopentyl)sulfamate as a yellow solid.

Example 3

Preparation of [S-(R*,R*)]-3,6-anhydro-1,2-
dideoxy-1-[5-[4-[(5-nitro-2-thienyl)]phenyl]-2H-
tetrazol-2-yl]-D-allo-heptitol 7-(2-amino-3-methyl-
1-oxopentyl)sulfamate To a solution of 4-ethynylbenzonitrile (0.5 g), 2-bromo-5-nitrothiophene (0.9 g) and bis(triphenylphosphine) palladium dichloride (83 mg) in anhydrous dimethylformamide (4 ml) was added triethylamine (2.2 ml). The reaction mixture was stirred at room temperature for 3 days then ethyl acetate (200 ml) and saturated sodium chloride (200 ml) were added. The organic layer was dried over anhydrous sodium sulfate, filtered and evaporated to dryness. The crude solid was triturated with 1:1 dichloromethane/hexane followed by diethyl ether to give 4-[(5-nitro-2-thienyl)ethynyl] benzonitrile as a yellow solid.

To a solution of 4-[(5-nitro-2-thienyl)ethynyl]benzonitrile (0.6 g) and dibutyltin oxide (59 mg) in anhydrous toluene (30 ml) was added trimethylsilyl azide (0.5 ml). The reaction mixture was heated to reflux in the dark for 12 hours, then allowed to cool to room temperature. The reaction mixture was washed with saturated sodium bicarbonate (2×300 ml) and the combined aqueous layer was acidified to pH 1 with concentrated hydrochloric acid (30 ml). The acidified solution was washed with 1:1 ethyl acetate/tetrahydrofuran (500 ml) and the organic layer was dried over anhydrous sodium sulfate, filtered and evaporated to dryness to give 5-[4-[(5-nitro-2-thienyl)ethynyl]-phenyl]-1H-tetrazole as a yellow solid.

To a solution of [S-(R*,R*)]-3,6-anhydro-2-deoxy-4,5-O-(1-methylethylidene)-D-allo-heptitol 7-[2-[(1,1-dimethylethoxy)carbonylamino]-3-methyl-1-oxopentyl] sulfamate (0.8 g), triphenylphosphine (1.23 g) and 5-[4-[(5-nitro-2-thienyl)ethynyl]phenyl]-1H-tetrazole (0.7 g) in anhydrous tetrahydrofuran (30 ml) was added diisopropylazodicarboxylate (0.62 ml). The reaction mixture was stirred at room temperature for 12 hours then diluted with ethyl acetate (200 ml) and washed with 1M hydrochloric acid (100 ml), saturated sodium bicarbonate (200 ml) and 1M hydrochloric acid (100 ml). The organic layer was dried over anhydrous sodium sulfate, filtered and evaporated to dryness. The residue was purified by silica gel chromatography (2–4% methanol in dichloromethane) to give [S-(R*, R*)]-3,6-anhydro-1,2-dideoxy-4,5-O-(1-methylethylidene)-1-[5-[4-[(5-nitro-2-thienyl)ethynyl]phenyl]-2H-tetrazol-2-yl]-D-allo-heptitol 7-[2-[(1,1-dimethylethoxy)-carbonylamino]-3-methyl-1-oxopentyl]sulfamate as a yellow foam.

To a solution of trifluoroacetic acid (5 ml) and water (2 ml) was added [S-(R*,R*)]-3,6-anhydro-1,2-dideoxy-4,5-O-(1-methylethylidene)-1-[5-[4-[(5-nitro-2-thienyl)ethynyl] phenyl]-2H-tetrazol-2-yl]-D-allo-heptitol 7-[2-[(1,1-dimethylethoxy)-carbonylamino]-3-methyl-1-oxopentyl]

sulfamate (0.8 g). The mixture was stirred at room temperature for 2 hours then evaporated to dryness. The residue was recrystallized from methanol and a few drops of water. The yellow solid obtained was filtered and washed with diethyl ether (20 ml) to give [S-(R*,R*)]-3,6-anhydro-1,2-dideoxy-1-[5-[4-[(5-nitro-2-thienyl)ethynyl]phenyl]-2H-tetrazol-2-yl]-D-allo-heptitol 7-(2-amino-3-methyl-1-oxopentyl)sulfamate.

Example 4

Preparation of [S-(R*,R*)]-2,5-anhydro-1-deoxy-1-[5-(4-phenoxyphenylmethyl)-2H-tetrazol-2-yl]-D-allitol 6-(2-amino-3-methyl-1-oxopentyl)sulfamate To a solution of 1,4-anhydro-2,3,5-O-benzoyl-1-cyano-1-deoxy-D-ribose (21.5 g; see K. Utimoto, et al., *Tetrahedron Lett.*, 23 (2), 237–238, 1982) in methanol (150 ml) was added sodium methoxide (10 ml, 2M in methanol). The mixture was stirred for 1.5 hours at room temperature then Amberlite® IR-120(+) resin (Rohm and Haas Company, Philadelphia, Pa.) was added until the pH was <3. The mixture was stirred for an additional 1 hour, then filtered and evaporated to dryness to afford 1,4-anhydro-1-carbomethoxy-1-deoxy-D-ribose as a light brown syrup.

To a solution of 1,4-anhydro-1-carbomethoxy-1-deoxy-D-ribose (1.43 g) in acetone (50 ml) was added 2,2-dimethoxypropane (1.1 ml) and camphorsulfonic acid (20 mg). The mixture was stirred at room temperature for 1 hour then additional 2,2-dimethoxypropane (1 ml) was added. After an additional 3 hours 2,2-dimethoxypropane (0.5 ml) was added and the reaction mixture was stirred an additional 1 day. The mixture was then evaporated to dryness, dissolved in ethyl acetate (100 ml) and washed with water (2×50 ml). The organic layer was then dried over anhydrous magnesium sulfate, filtered and evaporated to dryness. The residue was purified by silica gel chromatography (25% ethyl acetate in hexanes) to give 1,4-anhydro-1-carbomethoxy-1-deoxy-2,3-O-(1-methylethylidene)-D-ribose as a colorless oil.

To a solution of 1,4-anhydro-1-carbomethoxy-1-deoxy-2,3-O-(1-methylethylidene)-D-ribose (3.44 g) in anhydrous dimethylformamide (16 ml) was added imidazole (1.55 g) and tert-butyldimethylsilyl chloride (3.35 g). The mixture was stirred for 2.5 hours at room temperature, then ethyl acetate (150 ml) and water (100 ml) were added. The organic layer was separated, dried over anhydrous sodium sulfate, filtered and evaporated to dryness to give 1,4-anhydro-1-carbomethoxy-1-deoxy-5-O-[(1,1-dimethylethyl)dimethylsilyl]-2,3-O-(1methylethylidene)-D-ribose as a colorless syrup.

To a solution of 1,4-anhydro-1-carbomethoxy-1-deoxy-5-O-[(1,1-dimethylethyl)-dimethylsilyl]-2,3-O-(1-methylethylidene)-D-ribose (4.58 g) in anhydrous tetrahydrofuran at 0° C. was added lithium aluminum hydride (0.71 g). The mixture was stirred for 1.5 hours at 0° C. then quenched by dropwise addition of 1M hydrochloric acid (2 ml). Diethyl ether (2×100 ml) and saturated potassium sodium tartrate tetrahydrate (Rochelle salt, 2×50 ml) were then added to the mixture. The organic layer was separated, dried over anhydrous sodium sulfate, filtered and evaporated to dryness to give 2,5-anhydro-6-0-[(1,1-dimethylethyl) dimethylsilyl]-3,4-O-(1-methylethylidene)-D-allitol as a colorless syrup.

To a solution of 4-phenoxyphenylacetonitrile (1.16 g) in anhydrous toluene (30 ml) was added trimethylsilylazide (1.1 ml) and dibutyltin oxide (0.19 g). The mixture was heated to reflux for 19 hours then allowed to cool to room temperature. The reaction mixture was then added to 1M sodium hydroxide (100 ml) and washed with diethyl ether (3×50 ml). The aqueous layer was acidified with concentrated hydrochloric acid (30 ml) then washed with 5:1 ethyl acetate/tetrahydrofuran (60 ml) and ethyl acetate (2×50 ml). The combined organic layer was dried over anhydrous sodium sulfate, filtered and evaporated to give 5-(4-phenoxyphenylmethyl)-1H-tetrazole as a white solid.

To a solution of 2,5-anhydro-6-O-[(1,1-dimethylethyl) dimethylsilyl]-3,4-O-(1-methylethylidene)-D-allitol (0.83 g) in anhydrous tetrahydrofuran (10 ml) was added 5-(4-phenoxyphenylmethyl)-1H-tetrazole (0.64 g) diisopropylazodicarboxylate (0.95 ml) and triphenylphosphine (1.37 g). The mixture was stirred at room temperature under nitrogen for 21.5 hours, evaporated to dryness and the residue purified by silica gel chromatography (10–30% ethyl acetate in hexanes) to give 2,5-anhydro-1-deoxy-6-O-[(1,1-dimethylethyl)dimethylsilyl]-3,4-O-(1-methylethylidene)-1-[5-(4-phenoxyphenylmethyl)-2H-tetrazol-2-yl]-D-allitol.

To a solution of 2,5-anhydro-1-deoxy-6-O-[(1,1-dimethylethyl)dimethylsilyl]-3,4-O-(1-methylethylidene)-1-[5-(4-phenoxyphenylmethyl)-2H-tetrazol-2-yl]-D-allitol (1.35 g) in anhydrous tetrahydrofuran (20 ml) was added a solution of 1M tetrabutylammonium fluoride in tetrahydrofuran (8 ml). The reaction mixture was stirred at room temperature for 21 hours then added to ethyl acetate (100 ml) and water (50 ml). The organic layer was washed with saturated sodium chloride (2×25 ml), dried over anhydrous sodium sulfate, filtered and evaporated to dryness. The residue was then purified by silica gel chromatography (25–100% ethyl acetate in hexanes) to produce 2,5-anhydro-1-deoxy-3,4-O-(1-methylethylidene)1-[5-(4-phenoxyphenylmethyl)-2H-tetrazol-2-yl]-D-allitol as a colorless oil.

To a solution of 2,5-anhydro-1-deoxy-3,4-O-(1-methylethylidene)-1-[5-(4-phenoxyphenylmethyl)-2H-tetrazol-2-yl]-D-allitol (668 mg) in anhydrous dichloromethane (20 ml) was added triethylamine (1.1 ml) and phenylmethoxycarbonylsulfamoyl chloride (0.67 g). The mixture was stirred at room temperature under nitrogen for 1 day before being evaporated to dryness. The residue obtained was purified by silica gel chromatography (2–6% methanol in dichloromethane) to furnish 2,5-anhydro-1-deoxy-3,4-O-(1-methylethylidene)-1-[5-(4-phenoxyphenylmethyl)-2H-tetrazol-2-yl]-D-allitol 6-O-(phenylmethoxycarbonyl)sulfamate as a colo To a solution of 2,5-anhydro-1-deoxy-3,4-O-(1-methylethylidene)-1-[5-[4-(phenoxy)phenylmethyl]-2H-tetrazol-2-yl]-D-allitol 6-O-(phenylmethoxycarbonyl) sulfamate (0.6 g) in 1:1 ethanol/methanol (60 ml) was added 10% palladium on carbon (120 mg). The mixture was stirred under 1 atmosphere of hydrogen gas at room temperature for 6 hours then filtered through Celite® (diatomaceous earth, Johns-Manville, New York, N.Y.) and evaporated to dryness to give 2,5-anhydro-1-deoxy-3,4-O-(1-methylethylidene)-1-[5-(4-phenoxyphenylmethyl)-2H-tetrazol-2-yl]-D-allitol 6-sulfamate as an oil.

To a solution of 2,5-anhydro-1-deoxy-3,4-O-(1-methylethylidene)-1-[5-(4-phenoxyphenylmethyl)-2H-tetrazol-2-yl]-D-allitol 6-sulfamate (385 mg) in anhydrous dichloromethane (10 ml) was added 4-dimethylaminopyridine (289 mg), N-tert-butoxycarbonyl-2(S),3(S)-isoleucine (251 mg) and ethyl-3-(3-dimethylamino)propylcarbodiimide hydrochloride (205 mg). The mixture was stirred at room temperature for 7 hours then added to ethyl acetate (200 ml) and washed with 1M hydrochloric acid (2×50 ml), saturated sodium bicarbonate (2×50 ml), and saturated sodium chloride (2×50 ml). The organic layer was then dried over anhydrous sodium sulfate, filtered and evaporated to dryness. The residue obtained was then purified by silica gel chromatography (1–5% methanol in dichloromethane) to give [S-(R*,R*)]-2,5-anhydro-1-deoxy-3,4-O-(1-methylethylidene)-1-[5-(4-phenoxyphenylmethyl)-2H-tetrazol-2-yl]-D-allitol 6-[2-[(1,1-dimethylethoxy)-carbonylamino]-3-methyl-1-oxopentyl]sulfamate as a colorless foam.

[S-(R*,R*)]-2,5-anhydro-1-deoxy-3,4-O-(1-methylethylidene)-1-[5-(4-phenoxyphenylmethyl)-2H-tetrazol-2-yl]-D-allitol 6-[2-[(1,1-dimethylethoxy)carbonylamino]-3-methyl-1-oxopentyl]sulfamate (430 mg) was added to a mixture of trifluoroacetic acid and water 1:1 (10 ml) and stirred at room temperature for 5 minutes. Water (0.1 ml) was then added and the mixture was stirred for an additional 1 hour. Methanol (10 ml) was added and the mixture was evaporated to dryness. The residue was purified by silica gel chromatography (6–15% methanol in dichloromethane) to give [S-(R*,R*)]-2,5-anhydro-1-deoxy-1-[5-(4-phenoxyphenylmethyl)-2H-tetrazol-2-yl]-D-allitol 6-(2-amino-3-methyl-1-oxopentyl)-sulfamate as a white solid.

TABLE I

| # | Structure | Mass Spectrum | General Procedure |
|---|-----------|---------------|-------------------|
| I | 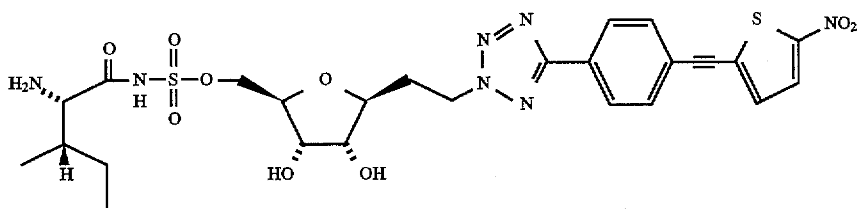 | Calc for M + Cs 782.0679 Obtained 782.0658 | 1 |
| II | 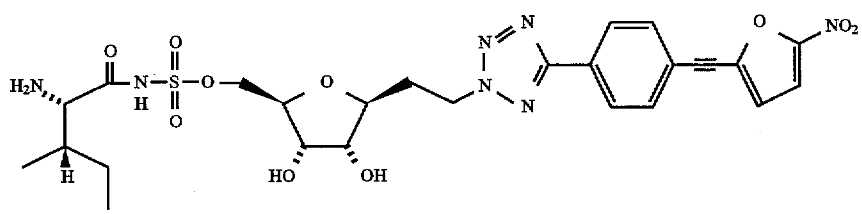 | Calc for M + Cs 766.0907 Obtained 766.0929 | 1 |
| III | 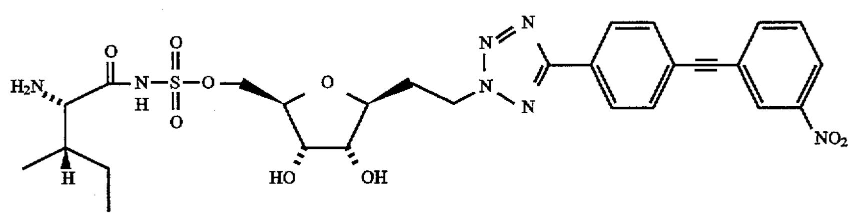 | Calc for M + Cs 776.1115 Obtained 776.1135 | 1 |
| IV | 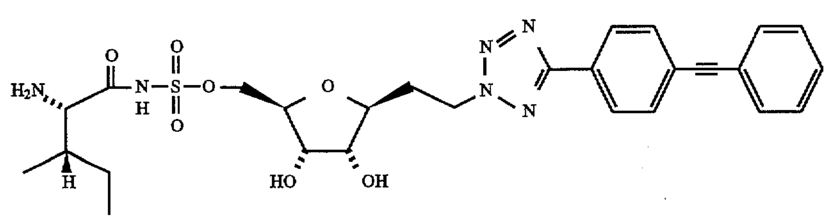 | Calc for M − H + 2Cs 863.0240 Obtained 863.0214 | 1 |
| V | 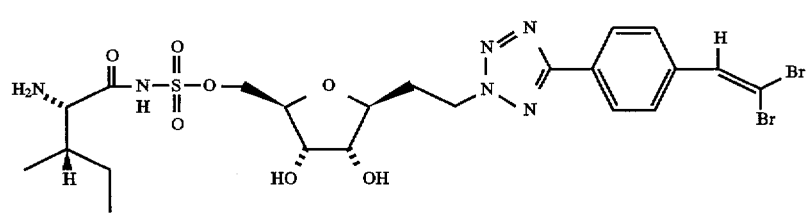 | Calc for M + Cs 812.9318 Obained 812.9339 | 1 |

TABLE I-continued
| # | Structure | Mass Spectrum | General Procedure |
|---|---|---|---|
| VI | 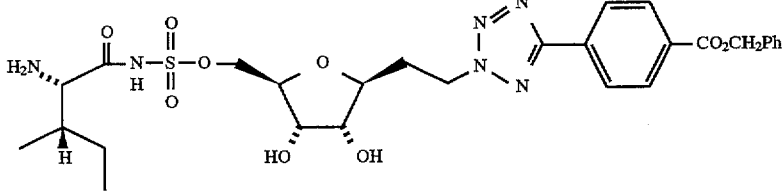 | Calc for M + Cs 765.1319 Obtained 765.1345 | 1 |
| VII | 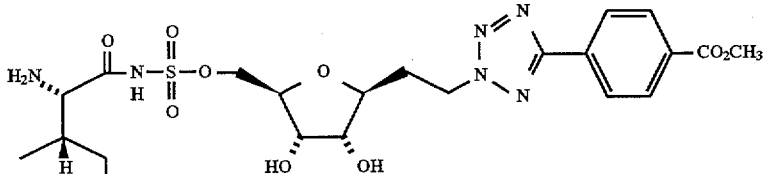 | Calc for M + Cs 689.1006 Obtained 689.1025 | 1 |
| VIII | 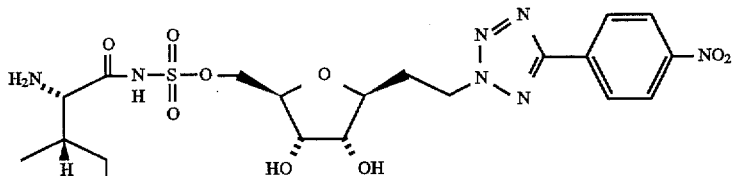 | Calc for M + Cs 676.0802 Obtained 676.0834 | 1 |
| IX | 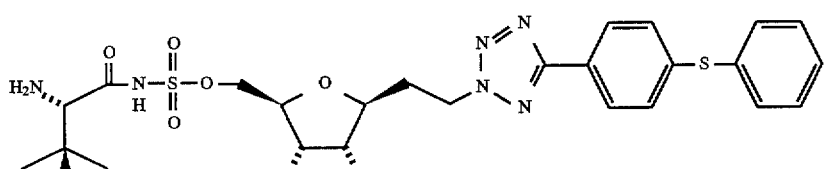 | Calc for M + Cs 739.0985 Obtained 739.1018 | 1 |
| X | 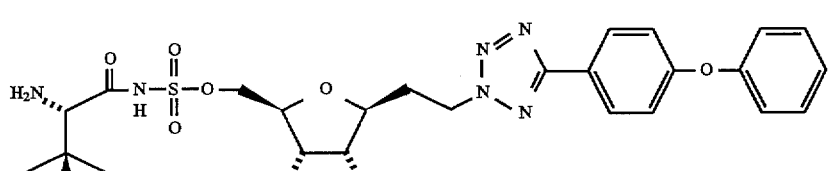 | Calc for M + Cs 723.1213 Obtained 723.1181 | 1 |
| XI | 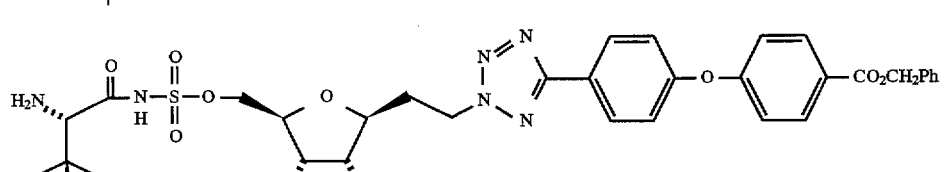 | Calc for M + Cs 857.1581 Obtained 857.1557 | 1 |
| XII | 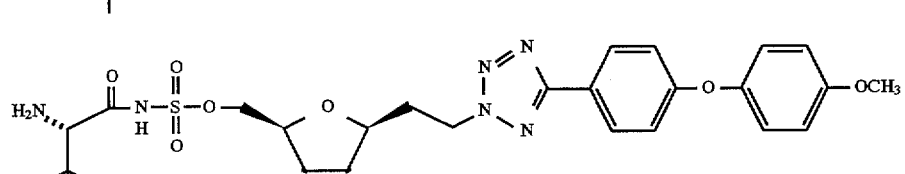 | Calc for M + Cs 753.1319 Obtained 753.1355 | 1 |

TABLE I-continued
| # | Structure | Mass Spectrum | General Procedure |
|---|---|---|---|
| XIII | 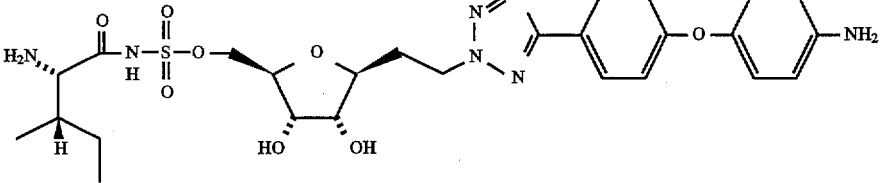 | Calc for M + Cs 738.1322 Obtained 738.1343 | 1 |
| XIV | 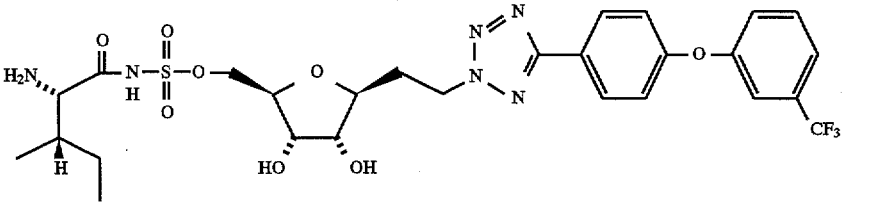 | Calc for M + Cs 791.1087 Obtained 791.1067 | 1 |
| XV | 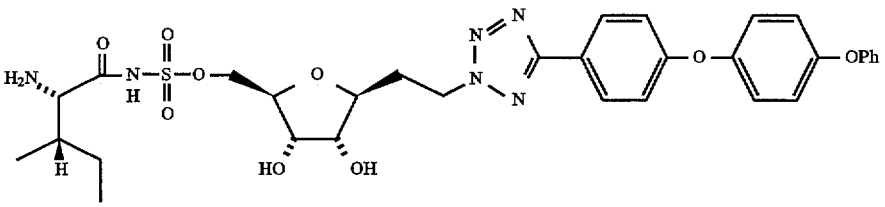 | Calc for M + Cs 815.1475 Obtained 815.1441 | 1 |
| XVI | 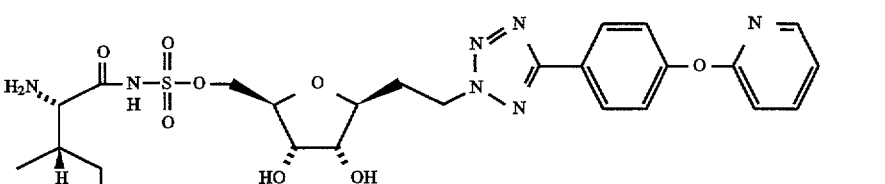 | Calc for M + Cs 724.1166 Obtained 724.1187 | 1 |
| XVII | 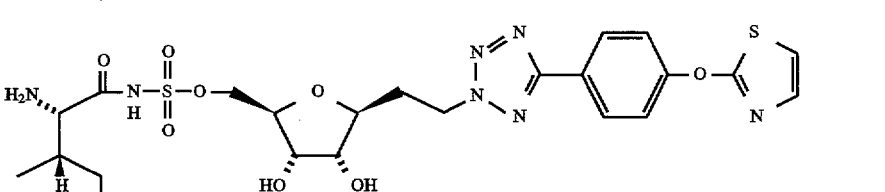 | Calc for M + Cs 730.0730 Obtained 730.0761 | 1 |
| XVIII | 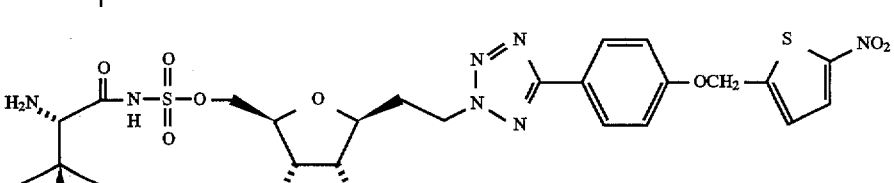 | Calc for M + H 656.1809 Obtained 656.1803 | 1 |
| XIX | 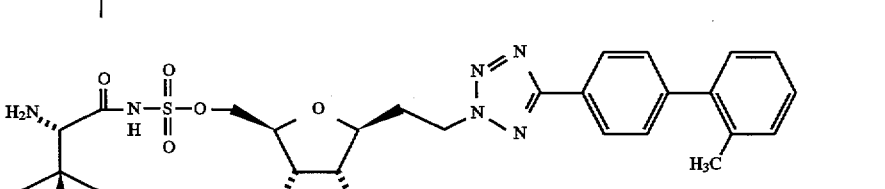 | Calc for M + Cs 721.1421 Obtained 721.1456 | 1 |

TABLE I-continued
| # | Structure | Mass Spectrum | General Procedure |
|---|---|---|---|
| XX | 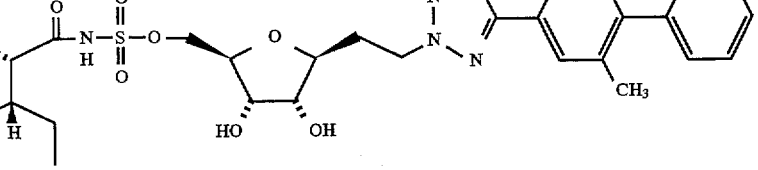 | Calc for M + Cs 721.1421 Obtained 721.1453 | 1 |
| XXI | 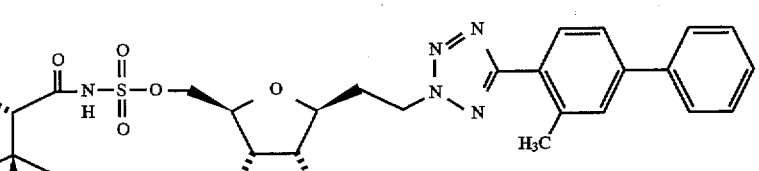 | Calc for M + Cs 721.1421 Obtained 721.1425 | 1 |
| XXII | 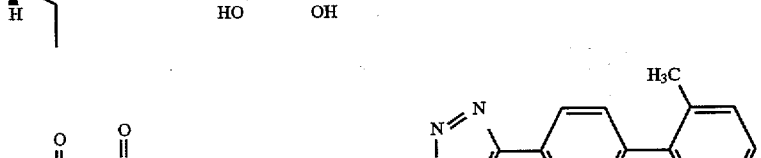 | Calc for M + Cs 735.1577 Obtained 735.1542 | 1 |
| XXIII | 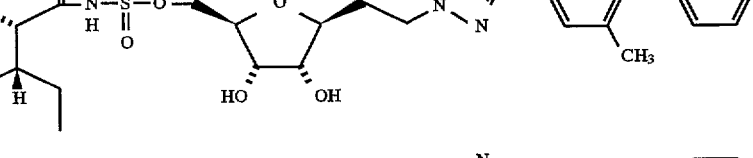 | Calc for M + H 611.2100 Obtained 611.1200 | 1 |
| XXIV | 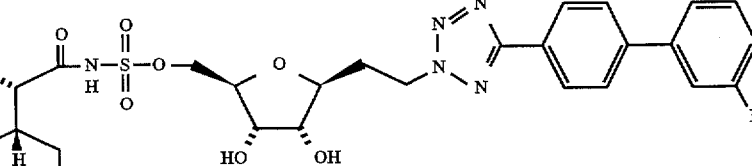 | Calc for M + Cs 715.1639 Obtained 715.1607 | 1 |
| XXV | 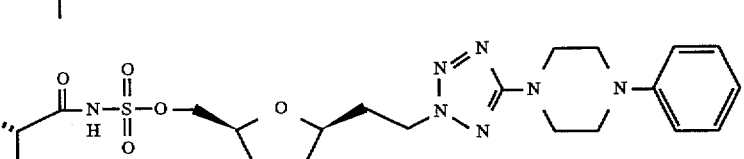 | Calc for M + Cs 709.1169 Obtained 709.1199 | 1 |
| XXVI | 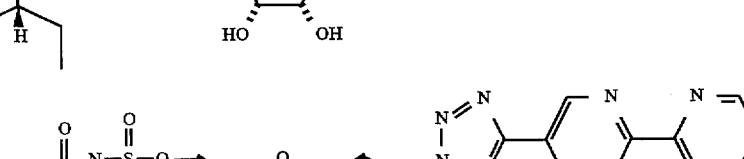 | Calc for M + Cs 725.1006 Obtained 725.0981 | 1 |

TABLE I-continued

| # | Structure | Mass Spectrum | General Procedure |
|---|---|---|---|
| XXVII | 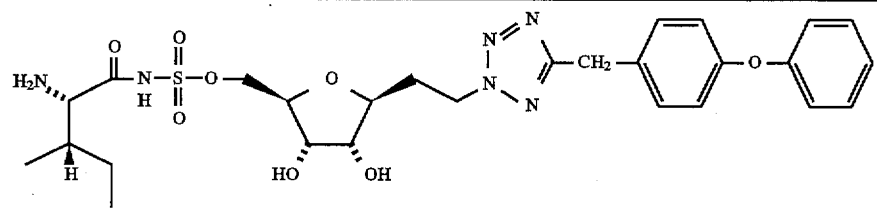 | Calc for M + Cs 723.1213 Obtained 723.1225 | 2 |
| XXVIII | 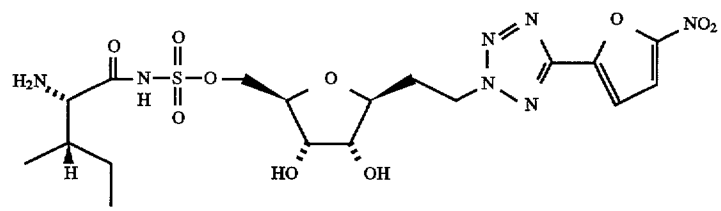 | Calc for M + Cs 666.0594 Obtained 666.0578 | 1 |
| XXIX | 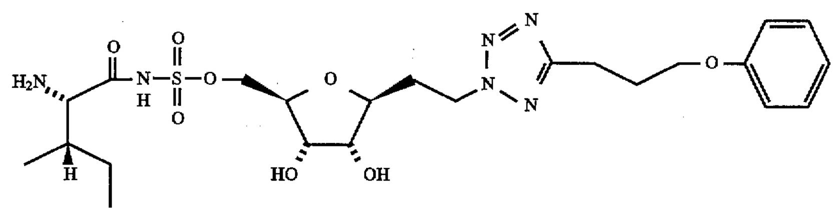 | Calc for M + Cs 689.1370 Obtained 689.1388 | 1 |
| XXX | 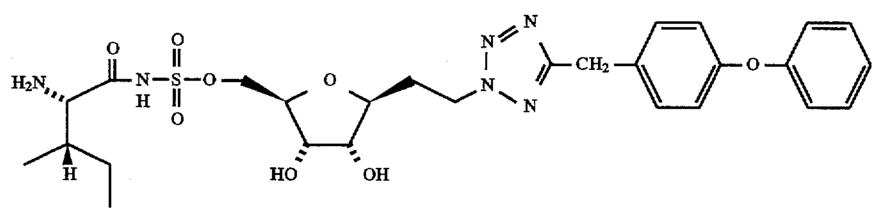 | Calc for M + Cs 737.1370 Obtained 737.1365 | 1 |
| XXXI | 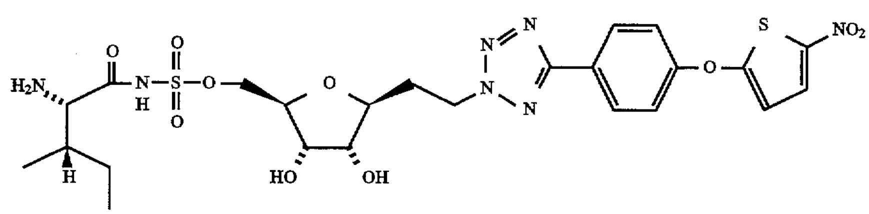 | Calc for M + Cs 774.0628 Obtained 774.0611 | 1 |

BIOLOGICAL EVALUATION

Enzymatic activity

The extent of aminoacylation of tRNA with isoleucine catalyzed by isoleucyl-tRNA synthetase enzyme was measured by monitoring the incorporation of [3H] isoleucine into trichloroacetic acid-precipitable tRNA in the presence of a compound of Formula I, as compared with activity in the absence of inhibitor. The isoleucyl-tRNA synthetase enzymes are well known in the prior art and can be obtained and purified by known methods (for example see: D. Kern et at., *Biochimie*, 61, 1257–1272 (1979) and J. Gilbart et al., *Antimicrobial Agents and Chemotherapy*, 37 (1), 32–38 (1993)).

Isoleucyl-tRNA synthetase enzyme (0.08–2.0 nM, preferably, 0.4 nM) was first pre-incubated at 25° C. with 0.05 mg/ml bovine serum albumin, 10 mM DTT, 2.5% dimethyl sulfoxide, with or without a compound of Formula I, for 20 minutes. At this point a substrate solution (a solution containing the following: ATP, [3H]isoleucine, tRNA, HEPES, magnesium chloride, and potassium chloride) was added to give a final concentration of 0.0286 mg/ml bovine serum albumin, 5.7 mM DTT, 4 mM ATP, 5–20 μM [3H] isoleucine (1–15 Ci/mmol), 90 μM crude tRNA or 2 μM isoleucine specific tRNA, 1.4% dimethyl sulfoxide, 30 mM HEPES (pH 7.5), 10 mM magnesium chloride, and 50 mM potassium chloride and incubated at 25° C. Aliquots were removed at selected times (e.g. 5, 10, 20 minutes) and applied to 3MM filter paper discs (Whatman) and then dropped into 5% (wt/vol) trichloroacetic acid for >5 minutes. Filters were washed for three 10-minute periods in 5% trichloroacetic acid, rinsed in 95% ethanol and diethyl ether, and radioactivity was measured with Betafluor™ (National Diagnostics) by liquid scintillation counting.

Inhibitor activity is reported in Table II as an $IC_{50}$ value (inhibitor concentration causing 50% inhibition of enzyme activity) per a known amount of active enzyme. In the case of irreversible inhibitors (1:1 stoichiometry) these values are 50% of the active enzyme concentration. The $IC_{50}$ (in nM, E. coli) values of representative compounds of the present invention are listed in the second column of Table II.

Whole cell antimicrobial screens

Compounds were tested for antimicrobial activity against a panel of organisms according to standard procedures described by the National Committee for Clinical Laboratory Standards (NCCLS document M7-A3, Vol. 13, No. 25, 1993/NCCLS document M27-P, Vol. 12, No. 25, 1992). Compounds were dissolved in 100% dimethyl sulfoxide and were diluted to the final reaction concentration (0.1 µg/mL–500 µg/mL) in microbial growth media. In al cases the final concentration of dimethyl sulfoxide incubated with cells is less than or equal to 1%. For minimum inhibitory concentration (MIC) calculations, 2-fold dilutions of compounds were added to wells of a microtiter plate containing $5 \times 10^4$ bacteria or fungal cells in a final volume of 100 lambda of an appropriate media (Mueller-Hinton Broth; Haemophilus Test Media; Mueller-Hinton Broth+5% Sheep Blood; or RPMI 1690). Plates were incubated overnight at an appropriate temperature (30° C.–37° C.) and optical densities (measure of cell growth) were measured using a commercial plate reader. The MIC value is defined as the lowest compound concentration inhibiting growth of the test organism. The MIC (in µg/ml) values of representative compounds of the present invention are listed in Table II.

In light of the importance attributed to the adenine ring of related compounds by Brown and coworkers [see P. Brown et al. poster presented at the 16th International tRNA Workshop, Madison, Wis., May 27 to Jun. 1, 1995], one would not have expected the substantial biological activity of the compounds of the present invention as reported in Table II. Brown teaches that the removal of the adenine portion of tyrosinyl adenylate or replacement of the adenine moiety with naphthyl, results in a 1000 fold decrease in activity of these compounds.

TABLE II

MINIMUM INHIBITORY CONCENTRATION

| # | IC50 E.Coli. IleRS | S. aureus ATCC 6538P | S. aureus ATCC 14154 | S. epidermidis ATCC 33501 | S. saprophyticus ATCC 35552 | S. pyogenes ATCC 8668 | E. faecium ATCC 6569 | E. faecalis ATCC 33011 | B. subtilis ATCC 6633 | H. influenza ATCC 49247 | K. pneumonia ATCC 4352 | C. albicans ATCC 10231 | M. catarrhalis ATCC 25240 | S. pneumonia ATCC 49619 |
|---|---|---|---|---|---|---|---|---|---|---|---|---|---|---|
| I | 1.3 nM | 1 | 5 | 1 | 2 | | >500 | >500 | | | | >500 | | |
| II | 1 nM | 4 | 8 | 1 | 8 | 16 | 64 | 256 | | 16 | | 100 | | 16 |
| III | 3 nM | 50 | 50 | 1 | 5 | | >500 | >500 | | | | >500 | | |
| IV | 4.5 nM | 10 | 100 | 2 | 10 | | >500 | >500 | 25 | | 50 | >200 | 5 | |
| V | 11 nM | 50 | 100 | 25 | 25 | | 100 | 500 | | | | 500 | | |
| VI | 7.5 nM | 25 | 50 | 5 | 25 | >5 | 100 | >500 | | | | >500 | | |
| VII | 0.53 nM | 100 | 500 | 10 | 50 | | 100 | >500 | | | | >500 | | |
| VIII | 0.5 nM | 500 | 500 | 10 | 100 | | 500 | >500 | | | | >500 | | |
| IX | 5 nM | 25 | 50 | 5 | 25 | 0.5 | 10 | 500 | | | | >500 | | |
| X | 1.3 nM | 10 | 25 | 2 | 5 | 0.5 | 10 | 300 | 10 | 100 | 50 | >500 | 25 | 25 |
| XI | 109 nM | 10 | 25 | 5 | 10 | 5 | 25 | >500 | | 25 | | 500 | | 50 |
| XII | 3 nM | 25 | 50 | <5 | 25 | | 10 | 500 | | | | 500 | | |
| XIII | 0.4 nM | 50 | 100 | 10 | 25 | | 25 | >500 | | | | >500 | | |
| XIV | 1.7 nM | 10 | 25 | 5 | 10 | | 10 | 100 | | | | >500 | | |
| XV | 1.8 nM | 10 | 10 | 5 | 10 | | 25 | >500 | | | | >500 | | |
| XVI | 0.7 nM | 100 | 100 | 25 | 50 | | 50 | 500 | | | | >500 | | |
| XVII | 1 nM | 100 | 500 | 25 | 50 | | 50 | >500 | | | | >500 | | |
| XVIII | 0.6 nM | 5 | 25 | 5 | 5 | 2 | >500 | >500 | | | | 100 | | |
| XIX | 5.3 nM | 50 | 50 | 25 | 25 | | 200 | 300 | 50 | | 100 | 500 | 50 | |
| XX | 0.6 nM | 50 | 50 | 25 | 25 | | 100 | 500 | 50 | >500 | 50 | >500 | 25 | |
| XXI | 0.5 nM | 100 | 500 | 50 | 50 | 10 | 500 | >500 | 100 | | 100 | >500 | <50 | 25 |
| XXII | 11 nM | 25 | 25 | 5 | 10 | | 100 | >500 | 25 | | 100 | >500 | 50 | |
| XXIII | 2.9 nM | 50 | 100 | 10 | 25 | | 100 | 200 | 50 | | 100 | 10 | | |
| XXIV | 1.3 nM | 400 | >400 | 50 | 400 | | 400 | >400 | 400 | | 400 | 500 | 400 | |
| XXV | 0.5 nM | 500 | 100 | 25 | 50 | | >500 | >500 | >500 | | >500 | >500 | | |
| XXVI | 1.5 nM | 500 | 500 | 50 | 100 | | 500 | >500 | | | | >500 | | |
| XXVII | 135 nM | >500 | >500 | >500 | >500 | | >500 | >500 | | | | >500 | | |
| XXVIII | 8.8 nM | 128 | 128 | 32 | >128 | | >128 | >128 | | | | 500 | | |
| XXIX | 0.3 nM | 500 | >500 | 25 | 500 | | >500 | >500 | | | | >500 | | |
| XXX | 2.7 nM | 100 | 500 | 25 | 100 | | 100 | 500 | | | | >200 | | |
| XXXI | 1.3 nM | 5 | 10 | 5 | 2 | 4 | 100 | >500 | | | | | | |

In Vivo Efficacy
Mouse Protection Test Against Wild Type *Streptococcus pyogenes*

The mouse protection test is an industry standard for measuring the efficacy of a test compound in vivo [for examples of this model see J. J. Clement, et al., *Antimicrobial Agents and Chemotherapy*, 38 (5), 1071–1078, (1994)]. As exemplified below, this test was used to show the in vivo efficacy of the compounds of the present invention against bacteria.

The in vivo antibacterial activity of compound X was established by infecting female CD-1 mice (Charles River Lab, Massachusettes) weighing 20–24 g intraperitoneally with *Streptococcus pyogenes* inoculum. The inoculum was prepared from *Streptococcus pyogenes* (ATCC 8668) which was cultured in brain heart infusion broth (Baltimore Biological Laboratories, Maryland) at 37° C. for 18 hr, and then 0.1 ml of the overnight culture was diluted with the medium to 5.0 ml for reading its OD at 600 nm (0.017). The turbidity of a 0.5 McFarland standard is equivalent to $OD_{600}$ 0.1, or 108 cfu/ml. Then, $8 \times 10^5$ cfu of the bacteria (940 μl of 1:1000 overnight culture) was added to 20 ml of phosphate buffered saline (Sigma P-0261) containing 5% hog gastric mucin (Sigma M-2378). All animals were injected with 0.5 ml of the inoculum, equivalent to $2 \times 10^4$ cfu/mouse which is the dose causing ~100% death of the animals without treatment.

Compound X (50 mg) was dissolved in 5.0 ml of 0.05M Tris.HCl (pH 8.8) to give a solution of 10 mg/ml. This solution was serially diluted with 0.05 M Tris.HCl by 5-fold (1.0 ml to 5.0 ml) to give 2, 0.4 and 0.08 mg/ml solutions. The known antibiotic erythromycin (Sigma E-6376, in phosphate buffered saline, 1 mg/ml, pH 7.0) was used as a positive control. All the solutions were filtered with 0.2 μm Nalgene syringe filter. Immediately after the bacterial inoculation, group 1 animals were subcutaneously (sc) injected with 0.05M Tris.HCl (no antibiotic) and groups 2 to 5 were given compound X sc at 0.8, 4, 20, and 100 mg/kg, respectively. Group 6 animals received erythromycin sc at 10 mg/kg. These injections were repeated once at 4 hours after the inoculation for the respective groups. The injection volume at each time was 10 ml per kilogram of body weight. The results of the in vivo efficacy test are summarized in Table III. The 50% protective dose ($PD_{50}$) is calculated on the basis of the number of mice surviving 7 days after inoculation.

TABLE III

Mouse Protection Test of Compound X Against *Streptococcus pyogenes*

| Dose (mg/kg, sc) | Number of mice | Number of Alive | Protective % |
|---|---|---|---|
| Negative control with buffer | 5 | 0 | 0 |
| 0.08 | 5 | 0 | 0 |
| 4 | 5 | 0 | 0 |
| 20 | 5 | 2 | 40 |
| 100 | 5 | 5 | 100 |
| Erythromycin 10 mg/kg | 5 | 5 | 100 |

$PD_{50} = 21.1$ (mg/kg) for compound X

Mouse Protection Test Against Multidrug Resistant *Streptococcus pyogenes*

The in vivo activity of compound X against multidrug resistant bacteria was established by infecting female CD-1 mice (Charles River Lab, Massachusettes) weighing 20–24 g intraperitoneally with multidrug resistant *Streptococcus pyogenes* inoculum. The inoculum was prepared from multidrug resistant *Streptococcus pyogenes* (resistant to erythromycin, tetracycline, and chloramphenicol, #OTTO 209 obtained from Dr. Pentti Huovinen, National Public Health Institute, Finland) which was cultured in brain heart infusion broth (Baltimore Biological Laboratories, Maryland) at 37° C. for 2 hr, and then 0.1 ml of the culture was diluted with the medium to 1.0 ml for reading its OD at 600 nm (0.12). The turbidity of a 0.5 McFarland standard is equivalent to $OD_{600}$ 0.1, or $10^8$ cfu/ml. Then, $4 \times 10^8$ cfu of the bacteria (333 μl was added to 20 ml of phosphate buffered saline (Sigma P-0261) containing 10 % hog gastric mucin (Sigma M-2378). All animals were injected with 0.5 ml of the inoculum, equivalent to $10^7$ cfu/mouse which is the dose causing ~100% death of the animals without treatment.

Compound X (60 mg) was dissolved in 6.0 ml of 0.05M Tris.HCl (pH 8.8) to give a solution of 10 mg/ml. This solution was serially diluted two times with 0.05M Tris.HCl by 5-fold (1.0 ml to 5.0 ml) to give 2 and 0.4 mg/ml solutions. The known antibiotic vancomycin HCl (Sigma V-2002, in normal saline, 1 mg/ml, pH 6.0–7.0) was used as a positive control. All the solutions were filtered with 0.2 μm Nalgene syringe filter. Immediately after the bacterial inoculation, group 1 animals were subcutaneously (sc) injected with 0.05M Tris.HCl (no antibiotic) and groups 2 to 4 were given compound X sc at 4, 20 and 100 mg/kg, respectively. Group 5 animals received vancomycin sc at 10 mg/kg. These injections were repeated once at 4 hours after the inoculation for the respective groups. The injection volume at each time was 10 ml per kilogram of body weight. The results of the multidrug resistant in vivo efficacy test are summarized in Table IV. The 50% protective dose ($PD_{50}$) is calculated on the basis of the number of mice surviving 7 days after inoculation.

TABLE IV

Mouse Protection Test of Compound X Against Multidrug Resistant *Streptococcus pyogenes*

| Dose (mg/kg, sc) | Number of mice | Number of Alive | Protective % |
|---|---|---|---|
| Negative control with buffer | 5 | 0 | 0 |
| 4 | 5 | 0 | 0 |
| 20 | 5 | 4 | 80 |
| 100 | 5 | 5 | 100 |
| Vancomycin 10 mg/kg | 5 | 5 | 100 |

$PD_{50} = 16.5$ (mg/kg) for compound X

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A compound of the Formula:

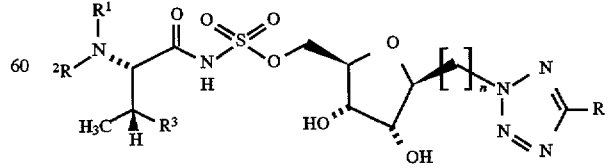

(a) wherein R is selected from the group consisting of amino, alkyl, aryl, cycloalkyl, alkoxy and aryloxy;

(b) wherein each of $R^1$ and $R^2$ is independently selected from the group consisting of hydrido, alkyl, aryl, carboalkoxy, alkylthiocarbonyl, carboxyamido, and acyl;

(c) wherein $R^3$ is selected from the group consisting of ethyl and methoxy;

(d) wherein n is a number selected from the group consisting of 1 and 2;

and pharmaceutically-acceptable salts thereof.

2. The compound of claim 1 wherein R is aryl.

3. The compound of claim 2 wherein n is 2.

4. The compound of claim 3 wherein each of $R^1$ and $R^2$ is hydrido and wherein $R^3$ is ethyl.

5. A compound of claim 4 of the Formula:

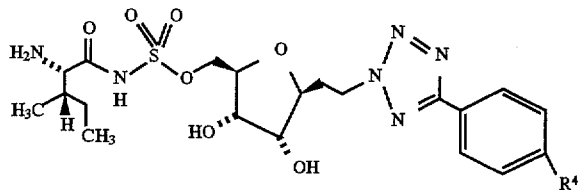

wherein $R^4$ is selected from the group consisting of alkyl, alkoxy and aryloxy.

6. The compound of claim 5 wherein $R^4$ is selected from the group consisting of alkyl, alkoxy and aryloxy, wherein the alkyl is an alkynyl, said alkynyl being substituted with at least one aryl substituent.

7. The compound of claim 6 selected from compounds, or a pharmaceutically-acceptable salt thereof, of the group consisting of [S-(R*,R*)]-3,6-anhydro-1,2-dideoxy-1-[5-[4-[(5-nitro-2-furyl)ethynyl]phenyl]-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-[4-[(5-nitro-2-thienyl)ethynyl]phenyl]-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-[4-(4-phenylethynylphenyl)-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-(4-phenoxyphenyl)-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-[4-(4-phenoxyphenoxy)phenyl]-2H-tetrazol-2-yl]-D-allo-heptitol 7-(2-amino-3-methyl-1-oxopentyl)sulfamate, and [S-(R*,R*)]-3,6-anhydro-1,2-dideoxy-1-[5-[4-(4-carboxymethylphenylphenoxy)phenyl]-2H-tetrazol-2-yl]-D-allo-heptitol 7-(2-amino-3-methyl-1-oxopentyl) sulfamate.

8. A pharmaceutical composition comprising a therapeutically-effective amount of an active compound and a pharmaceutically-acceptable carrier, said active compound selected from a family of compounds of the Formula:

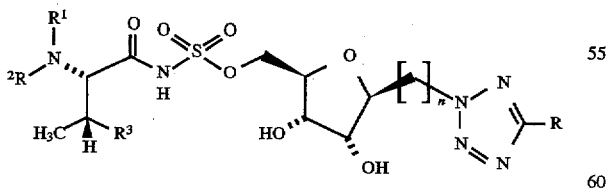

(a) wherein R is selected from the group consisting of amino, alkyl, aryl, cycloalkyl, alkoxy, and aryloxy;

(b) wherein each of $R^1$ and $R^2$ is independently selected from the group consisting of hydrido, alkyl, aryl, carboalkoxy, alkylthiocarbonyl, carboxyamido, and acyl;

(c) wherein $R^3$ is selected from the group consisting of ethyl and methoxy;

(d) wherein n is a number selected from the group consisting of 1 and 2;

and pharmaceutically-acceptable salts thereof.

9. The composition of claim 8 wherein R is aryl.

10. The composition of claim 9 wherein n is 2.

11. The composition of claim 10 wherein each of $R^1$ and $R^2$ is hydrido and wherein $R^3$ is ethyl.

12. The composition of claim 8 wherein said active compound is selected from a family of compounds of the Formula:

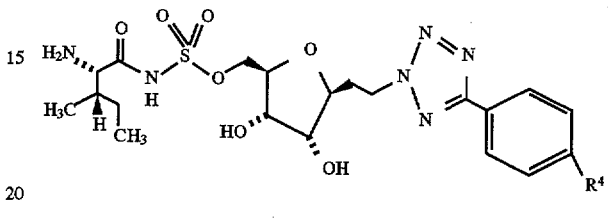

wherein $R^4$ is selected from the group consisting of alkyl, alkoxy and aryloxy.

13. The composition of claim 12 wherein $R^4$ is selected from the group consisting of alkyl, alkoxy and aryloxy, wherein the alkyl is an alkynyl, said alkynyl being substituted with at least one aryl substituent.

14. The composition of claim 13 wherein said active compound is selected from the compounds, or a pharmaceutically-acceptable salt thereof, of the group consisting of [S-(R*,R*)]-3,6-anhydro-1,2-dideoxy-1-[5-[4-[(5-nitro-2-furyl)ethynyl]phenyl]-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-[4-[(5-nitro-2-thienyl)ethynyl]phenyl]-2H-tetrazol-2yl]-D-allo-heptitol 7-(2-amino-3-methyl-1-oxopentyl)sulfamate, [S-(R*,R*)]-3,6-anhydro-1,2-dideoxy-1-[5-[4-(4-phenylethynylphenyl)-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-(4-phenoxyphenyl)-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-[4-(4-phenoxyphenoxy)phenyl]-2H-tetrazol-2yl]D-allo-heptitol 7-(2-amino-3-methyl-1-oxopentyl)sulfamate, and [S-(R*,R*)]-3,6-anhydro-1,2-dideoxy-1-[5-[4-(4-carboxymethylphenylphenoxy)phenyl]-2H-tetrazol-2-yl]-D-allo-heptitol 7-(2-amino-3-methyl-1-oxopentyl) sulfamate.

15. A method of treating a subject afflicted by or susceptible to an infection, wherein said subject is selected from the group consisting of a mammal, a plant and a culture, said method comprising administering to the subject a therapeutically-effective amount of the compound of the Formula:

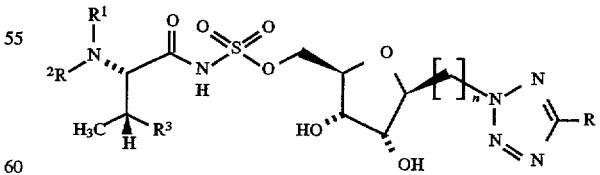

(a) wherein R is selected from the group consisting of amino, alkyl, aryl, cycloalkyl, alkoxy, and aryloxy;

(b) wherein each of $R^1$, and $R^2$ is independently selected from the group consisting of hydrido, alkyl, aryl, carboalkoxy, alkylthiocarbonyl, carboxyamido, and acyl;

(c) wherein $R^3$ is selected from the group consisting of ethyl and methoxy;

(d) wherein n is a number selected from the group consisting of 1 and 2;

and pharmaceutically-acceptable salts thereof.

16. The method of claim 15 wherein the infection is a bacterial or fungal infection.

17. The method of claim 15 wherein the subject is a mammal.

18. The method of claim 17 wherein the mammal is a human.

19. The method of claim 15 wherein R is aryl.

20. The method of claim 19 wherein n is 2.

21. The method of claim 20 wherein each of $R^1$ and $R^2$ is hydrido and wherein $R^3$ is ethyl.

22. The method of claim 15 wherein said compound is of the Formula:

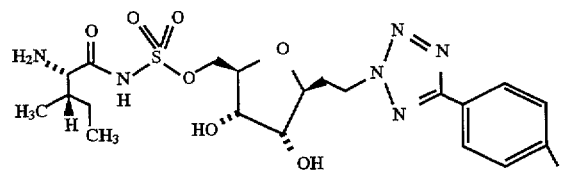

wherein $R^4$ is selected from the group consisting of alkyl, alkoxy and aryloxy.

23. The method of claim 22 wherein $R^4$ is selected from the group consisting of alkyl, alkoxy and aryloxy, wherein the alkyl is an alkynyl, said alkynyl being substituted with at least one aryl substituent.

24. The method of claim 23 wherein said compound is selected from the compounds, or a pharmaceutically-acceptable salt thereof, of the group consisting of [S-(R*,R*)]-3,6-anhydro-1,2-dideoxy-1-[5-[4-[(5-nitro-2-furyl)ethynyl]phenyl]-2H-tetrazol-2-yl]-D-allo-hepitol 7-(2-amino-3-methyl-1-oxopentyl)sulfamate, [S-(R*,R*)]-3,6-anhydro-1,2-dideoxy-1-[5-[4-[(5-nitro-2-thienyl)ethynyl]phenyl]-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-(4-phenylethynylphenyl)-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-(4-phenoxyphenyl)-2H-tetrazol-2-yl]-D-allo-heptitol 7-(2-amino-3-methyl-1-oxopentyl)sulfamate, [S-(R*,R*)]-3,6-anhydro-1,2-dideoxy-1-[5-[4-(4-phenoxyphenoxy)phenyl]-2H-tetrazol-2-yl]-D-allo-heptitol 7-(2-amino-3-methyl-1-oxopentyl)sulfamate, and [S-(R*,R*)]-3,6-anhydro-1,2-dideoxy-1-[5-[4-(4-carboxymethylphenylphenoxy)phenyl]-2H-tetrazol-2-yl]-D-allo-heptitol 7-(2-amino-3-methyl-1-oxopentyl)sulfamate.

25. A method of inhibiting an isoleucyl-tRNA synthetase comprising contacting said isoleucyl-tRNA synthetase with a compound as claimed in any of claims 1–7.

26. A method of inhibiting the growth of microorganisms, comprising exposing said organisms to a compound claimed in any of claims 1–7.

27. A compound of the Formula:

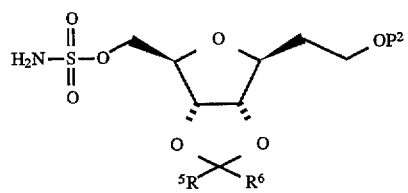

wherein:

(a) $P^2$ is selected from the group consisting of acyl, alkoxymethyl, aryloxymethyl, thiomethyl, arylmethyl, trialkylsilyl, triarylsilyl, diphenylmethylsilyl, diphenyl-tert-butylsilyl, (phenyldimethylsilyl)methoxymethyl, 2-(trimethylsilyl)ethoxymethyl, and tetrahydropyranyl;

(b) each of $R^5$ and $R^6$ is independently selected from the group consisting of hydrido, alkyl, aryl and cycloalkyl.

28. A compound of the Formula:

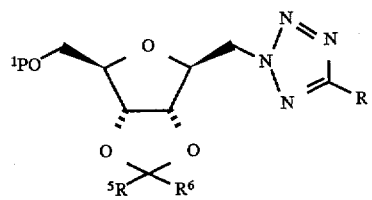

wherein:

(a) $P^1$ is selected from the group consisting of alkoxymethyl, aryloxymethyl, thiomethyl, arylmethyl, trialkylsilyl, triarylsilyl, diphenylmethylsilyl, diphenyl-tert-butylsilyl, (phenyldimethylsilyl)methoxymethyl, 2-(trimethylsilyl)ethoxymethyl, and tetrahydropyranyl;

(b) R is selected from the group consisting of amino, alkyl, aryl, cycloalkyl, alkoxy and aryloxy;

(c) each of $R^5$ and $R^6$ is independently selected from the group consisting of hydrido, alkyl, aryl and cycloalkyl.

29. A compound of the formula:

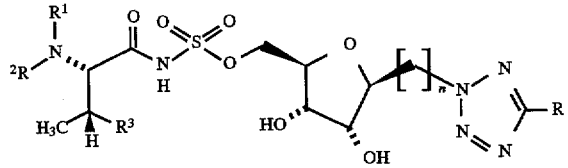

(a) wherein R is aryl;

(b) wherein each of $R^1$ and $R^2$ is independently selected from the group consisting of hydrido, alkyl, aryl, carboalkoxy, alkylthiocarbonyl, carboxyamido, and acyl;

(c) wherein $R^3$ is selected from the group consisting of ethyl and methoxy;

(d) wherein n is 1.

30. The compound of claim 29, wherein each of $R^1$ and $R^2$ is hydrido, and wherein $R^3$ is ethyl.

31. A compound having the formula:
[S-(R*,R*)]-3-,6-anhydro-1,2-dideoxy-1-[5-[4-[(5-nitro-2-furyl)ethynyl]phenyl]-2H-tetrazol-2-yl]-D-allo-heptitol 7-(2-amino-3-methyl-1-oxopentyl)sulfamate, or a pharmaceutically-acceptable salt thereof.

32. A compound having the formula:
[S-(R*,R*)]-3,6-anhydro-1,2-dideoxy-1-[5-[4-[(5-nitro-2-thienyl)-ethynyl]phenyl]-2H-tetrazol-2-yl]-D-alloheptitol 7-(2-amino-3-methyl-1-oxopentyl)sulfamate, or a pharmaceutically-acceptable salt thereof.

33. A compound having the formula:

[S-(R*,R*)]-3,6-anhydro-1,2-dideoxy-1-[5-(4-phenylethynylphenyl)-2H-tetrazol-2-yl]-D-allo-heptitol 7-(2-amino-3-methyl-1-oxopentyl)sulfamate, or a pharmaceutically-acceptable salt thereof.

34. A compound having the formula:

[S-(R*,R*)]-3,6-anhydro-1,2-dideoxy-1-[5-(4-phenoxyphenyl)-2H-tetrazol-2-yl]-D-allo-heptitol 7-(2-amino-3-methyl-1-oxopentyl)sulfamate, or a pharmaceutically-acceptable salt thereof.

35. A compound having the formula:

[S-(R*,R)]-3,6-anhydro-1,2-dideoxy-1-[5-[4-(4-phenoxyphenoxy)-phenyl]-2H-tetrazol-2-yl]-D-allo-heptitol 7-(2-amino-3-methyl-1-oxopentyl)sulfamate, or a pharmaceutically-acceptable salt thereof.

36. A compound having the formula:

[S-(R*,R*)]-3,6-anhydro-1,2-dideoxy-1-[5 -[4-(4-carboxymethylphenylphenoxy)-phenyl]-2H-tetrazol-2-yl]-D-allo-heptitol 7-(2-amino-3-methyl-1-oxopentyl)sulfamate or a pharmaceutically-acceptable salt thereof.

37. A pharmaceutical composition comprising a therapeutically-effective amount of the compound of claim 29 and a pharmaceutically-acceptable carrier.

38. A pharmaceutical composition comprising a therapeutically-effective amount of the compound of claim 30 and a pharmaceutically-acceptable carrier.

39. A pharmaceutical composition comprising a therapeutically-effective amount of a compound of claim 31, 32, 33, 34, 35, or 36, and a pharmaceutically-acceptable carrier.

40. A method of treating a subject afflicted by or susceptible to an infection, wherein said subject is selected from the group consisting of a mammal, a plant and a culture, wherein said infection is a bacterial infection or a fungal infection, said method comprising administering to the subject a therapeutically-effective amount of the compound of claim 29.

41. A method of treating a subject afflicted by or susceptible to an infection, wherein said subject is selected from the group consisting of a mammal, a plant and a culture, wherein said infection is a bacterial infection or a fungal infection, said method comprising administering to the subject a therapeutically-effective amount of the compound of claim 30.

42. A method of treating a subject afflicted by or susceptible to an infection, wherein said subject is selected from the group consisting of a mammal, a plant and a culture, wherein said infection is a bacterial infection or a fungal infection, said method comprising administering to the subject a therapeutically-effective amount of a compound of claim 31, 32, 33, 34, 35, or 36.

43. The method of claim 40 wherein the subject is a mammal.

44. The method of claim 41 wherein the subject is a mammal.

45. The method of claim 42 wherein the subject is a mammal.

46. The method of claim 43 wherein the mammal is a human.

47. The method of claim 44 wherein the mammal is a human.

48. The method of claim 45 wherein the mammal is a human.

49. A method of inhibiting an isoleucyl-t-RNA synthetase comprising contacting said isoleucyl-t-RNA synthetase with a compound as claimed in any of claims 29–36.

50. A method of inhibiting the growth of microorganisms, comprising exposing said organisms to a compound claimed in any of claims 29–36.

* * * * *